(12) United States Patent
Zhang et al.

(10) Patent No.: US 11,939,313 B2
(45) Date of Patent: *Mar. 26, 2024

(54) MOLECULE HAVING PESTICIDAL UTILITY, AND COMPOSITIONS, AND PROCESSES, RELATED THERETO

(71) Applicant: CORTEVA AGRISCIENCE LLC, Indianapolis, IN (US)

(72) Inventors: Yu Zhang, Carmel, IN (US); Tony K. Trullinger, Westfield, IN (US); Carla J. R. Klittich, Tucson, AZ (US); Ricky Hunter, Westfield, IN (US)

(73) Assignee: CORTEVA AGRISCIENCE LLC, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/113,206

(22) Filed: Dec. 7, 2020

(65) Prior Publication Data

US 2021/0087164 A1 Mar. 25, 2021

Related U.S. Application Data

(63) Continuation of application No. 16/416,382, filed on May 20, 2019, now Pat. No. 10,894,783.

(60) Provisional application No. 62/682,248, filed on Jun. 8, 2018.

(51) Int. Cl.
| | | |
|---|---|---|
| *C07D 401/04* | (2006.01) | |
| *A01N 25/04* | (2006.01) | |
| *A01N 25/14* | (2006.01) | |
| *A01N 43/58* | (2006.01) | |

(52) U.S. Cl.
CPC ........... *C07D 401/04* (2013.01); *A01N 25/04* (2013.01); *A01N 25/14* (2013.01); *A01N 43/58* (2013.01)

(58) Field of Classification Search
None
See application file for complete search history.

(56) References Cited

U.S. PATENT DOCUMENTS

| | | | |
|---|---|---|---|
| 8,815,271 B2 ‡ | 8/2014 | Yap | A61P 33/00 424/41 |
| 8,901,153 B2 ‡ | 12/2014 | Buysse | A61P 31/00 514/34 |
| 9,282,739 B2 ‡ | 3/2016 | Buysse | A01N 47/40 |
| 9,422,278 B2 ‡ | 8/2016 | Yap | A01N 43/76 |
| 9,549,560 B2 ‡ | 1/2017 | Walsh | C05G 3/60 |
| 9,591,857 B2 ‡ | 3/2017 | Buysse | A01N 43/647 |
| 9,708,288 B2 ‡ | 7/2017 | Buysse | A01N 47/36 |
| 10,894,783 B2 * | 1/2021 | Zhang | A01N 43/56 |
| 11,691,961 B2 | 7/2023 | Zhang et al. | |
| 2012/0110702 A1 ‡ | 5/2012 | Yap | C07D 409/14 800/29 |
| 2012/0238517 A1 | 9/2012 | Cassayre et al. | |
| 2013/0109566 A1 | 5/2013 | Niyaz et al. | |
| 2013/0288893 A1 | 10/2013 | Buysse et al. | |
| 2013/0291227 A1 ‡ | 10/2013 | Buysse | A01N 47/42 800/29 |
| 2013/0338367 A1 ‡ | 12/2013 | Numata | A01N 47/18 546/193 |
| 2014/0162874 A1 ‡ | 6/2014 | Yap | A01N 43/653 504/10 |
| 2015/0111733 A1 ‡ | 4/2015 | Walsh | C07D 401/04 504/100 |
| 2015/0112075 A1 | 4/2015 | Yang et al. | |
| 2015/0216169 A1 | 8/2015 | El Qacemi et al. | |
| 2016/0081342 A1 | 3/2016 | Popp et al. | |
| 2016/0318924 A1 ‡ | 11/2016 | Yap | A01N 43/76 |
| 2017/0267657 A1 ‡ | 9/2017 | Buysse | C07D 409/14 |
| 2018/0111924 A1 | 4/2018 | Webster et al. | |
| 2020/0055846 A1 ‡ | 2/2020 | Yap | A01N 25/00 |

FOREIGN PATENT DOCUMENTS

| | | | | |
|---|---|---|---|---|
| CL | 2013001228 A1 | 5/2013 | | |
| EP | 2674423 A1 ‡ | 12/2013 | ............ | A01N 43/56 |
| EP | 2674423 A1 | 12/2013 | | |
| EP | 3801026 B1 | 6/2022 | | |
| JP | 2014001205 A | 1/2014 | | |
| JP | 2014034539 A | 2/2014 | | |

(Continued)

OTHER PUBLICATIONS

Chapter II Demand for PCT/US2019/033099 aka WO 2019/236274 A1 (emailed).‡
International Preliminary Report on Patentability for PCT/US2019/033099 aka WO 2019/236274 A1.‡
Chapter II Demand for PCT/US2019/033099 aka WO 2019/236274 A1 (scanned).‡
International Search Report and Written Opinion for PCT/US2019/033099 aka WO 2019/236274 A1.‡

(Continued)

*Primary Examiner* — Erin E Hirt

(57) ABSTRACT

This disclosure relates to the field of molecules having pesticidal utility against pests in Phyla Arthropoda, Mollusca, and Nematoda, processes to produce such molecules, pesticidal compositions containing such molecules, and processes of using such pesticidal compositions against such pests. These pesticidal compositions may be used, for example, as acaricides, insecticides, miticides, molluscicides, and nematicides. This document discloses a molecule having the following formula.

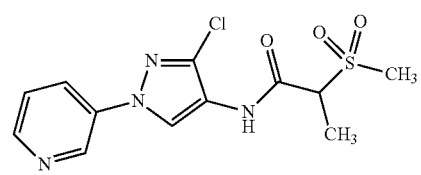

13 Claims, No Drawings

(56) References Cited

FOREIGN PATENT DOCUMENTS

| | | | |
|---|---|---|---|
| JP | 2014504267 | A | 2/2014 |
| JP | 2014111559 | A | 6/2014 |
| JP | 2014534217 | A | 12/2014 |
| JP | 2015518488 | T | 7/2015 |
| JP | 2015519320 | A | 7/2015 |
| JP | 2015164898 | A | 9/2015 |
| JP | 2015227325 | A | 12/2015 |
| JP | 2017137308 | A | 8/2017 |
| JP | 2021527052 | A | 10/2021 |
| JP | 2022122906 | A | 8/2022 |
| WO | 2012108511 | A1 | 8/2012 |
| WO | 2013062981 | A | 12/2014 |
| WO | 2016014664 | A1 | 1/2016 |
| WO | 2016128261 | A1 | 8/2016 |
| WO | 2017001252 | A1 | 1/2017 |
| WO | 2019236274 | A1 | 12/2019 |

OTHER PUBLICATIONS

Citybugs "Sucking pests" "https://citybugs.tamu.edu/factsheets/landscape/sapfeed/#:~:text=Common%20sap%2Dfeeding%20insects%20include,mouth%20parts%20feed%20on%20sap." No pagination, dated via wayback machine which has the page cached as of Nov. 13, 2010. (Year: 2010).‡

Citybugs "Sucking pests" https://citybugs.tamu.edu/factsheets/landscape/sapfeed/#:~:text=common%20sap%2Dfeeding%20insects%20include.mouth%20parts%20feed%20on%20sap. No pagination, dated via wayback machine which has the page cached as of Nov. 30, 2010. (Year: 2010).

Extended European Search Report for European Application No. 22170245.9, dated Sep. 19, 2022, 5 pages.

International Preliminary Report on Patentability for International Application No. PCT/US2022/013039, dated Jul. 20, 2023, 8 pages.

International Search Report and Written Opinion for International Application No. PCT/US2022/013039, dated May 13, 2022, 12 Pages.

\* cited by examiner
‡ imported from a related application

MOLECULE HAVING PESTICIDAL UTILITY, AND COMPOSITIONS, AND PROCESSES, RELATED THERETO

CROSS-REFERENCE TO RELATED APPLICATIONS

This application is a continuation of, and claims the benefit of, U.S. nonprovisional application Ser. No. 16/416,382, which was filed May 20, 2019, and which is now U.S. Pat. No. 10,894,783 B2 and claims the benefit of, and priority from, U.S. provisional application Ser. No. 62/682,248; which was filed on Jun. 8, 2018. The entire contents of the above-identified application are hereby incorporated by reference into this Application.

FIELD OF THIS DISCLOSURE

This disclosure relates to the field of molecules having pesticidal utility against pests in Phyla Arthropoda, Mollusca, and Nematoda, processes to produce such molecules, pesticidal compositions containing such molecules, and processes of using such pesticidal compositions against such pests. These pesticidal compositions may be used, for example, as acaricides, insecticides, miticides, molluscicides, and nematicides.

BACKGROUND OF THIS DISCLOSURE

"Many of the most dangerous human diseases are transmitted by insect vectors" (Rivero et al.). "Historically, malaria, dengue, yellow fever, plague, filariasis, louse-borne typhus, trypanomiasis, leishmaniasis, and other vector borne diseases were responsible for more human disease and death in the $17^{th}$ through the early $20^{th}$ centuries than all other causes combined" (Gubler). Vector-borne diseases are responsible for about 17% of the global parasitic and infectious diseases. Malaria alone causes over 800,000 deaths a year, 85% of which occur in children under five years of age. Each year there are about 50 to about 100 million cases of dengue fever. A further 250,000 to 500,000 cases of dengue hemorrhagic fever occur each year (Matthews). Vector control plays a critical role in the prevention and control of infectious diseases. However, insecticide resistance, including resistance to multiple insecticides, has arisen in all insect species that are major vectors of human diseases (Rivero et al.). Recently, more than 550 arthropod species have developed resistance to at least one pesticide (Whalon et al.). Furthermore, the cases of insect resistance continue to exceed by far the number of cases of herbicide and fungicide resistance (Sparks et al.).

Each year insects, plant pathogens, and weeds, destroy more than 40% of all food production. This loss occurs despite the application of pesticides and the use of a wide array of non-chemical controls, such as, crop rotations, and biological controls. If just some of this food could be saved, it could be used to feed the more than three billion people in the world who are malnourished (Pimental).

Plant parasitic nematodes are among the most widespread pests, and are frequently one of the most insidious and costly. It has been estimated that losses attributable to nematodes are from about 9% in developed countries to about 15% in undeveloped countries. However, in the United States of America a survey of 35 States on various crops indicated nematode-derived losses of up to 25% (Nicol et al.).

It is noted that gastropods (slugs and snails) are pests of less economic importance than other arthropods or nematodes, but in certain places, they may reduce yields substantially, severely affecting the quality of harvested products, as well as, transmitting human, animal, and plant diseases. While only a few dozen species of gastropods are serious regional pests, a handful of species are important pests on a worldwide scale. In particular, gastropods affect a wide variety of agricultural and horticultural crops, such as, arable, pastoral, and fiber crops; vegetables; bush and tree fruits; herbs; and ornamentals (Speiser).

Termites cause damage to all types of private and public structures, as well as to agricultural and forestry resources. In 2005, it was estimated that termites cause over US$50 billion in damage worldwide each year (Korb).

Consequently, for many reasons, including those mentioned above, there is an on-going need for the costly (estimated to be about US$256 million per pesticide in 2010), time-consuming (on average about 10 years per pesticide), and difficult, development of new pesticides (CropLife America).

CERTAIN REFERENCES CITED IN THIS DISCLOSURE

CropLife America, The Cost of New Agrochemical Product Discovery, Development & Registration, and Research & Development predictions for the Future, 2010.

Drewes, M., Tietjen, K., Sparks, T. C., High-Throughput Screening in Agrochemical Research, *Modern Methods in Crop Protection Research*, Part I, *Methods for the Design and Optimization of New Active Ingredients*, Edited by Jeschke, P., Kramer, W., Schirmer, U., and Matthias W., p. 1-20, 2012.

Gubler, D., Resurgent Vector-Borne Diseases as a Global Health Problem, Emerging Infectious Diseases, Vol. 4, No. 3, p. 442-450, 1998.

Korb, J., Termites, *Current Biology*, Vol. 17, No. 23, 2007.

Matthews, G., Integrated Vector Management: Controlling Vectors of Malaria and Other Insect Vector Borne Diseases, Ch. 1, p. 1, 2011.

Nicol, J., Turner S., Coyne, L., den Nijs, L., Hocksland, L., Tahna-Maafi, Z., Current Nematode Threats to World Agriculture, *Genomic and Molecular Genetics of Plant—Nematode Interactions*, p. 21-43, 2011.

Pimental, D., Pest Control in World Agriculture, *Agricultural Sciences*—Vol. II, 2009.

Rivero, A., Vezilier, J., Weill, M., Read, A., Gandon, S., Insect Control of Vector-Borne Diseases: When is Insect Resistance a Problem? *Public Library of Science Pathogens*, Vol. 6, No. 8, p. 1-9, 2010.

Sparks T. C., Nauen R., IRAC: Mode of action classification and insecticide resistance management, *Pesticide Biochemistry and Physiology* (2014) available online 4 Dec. 2014.

Speiser, B., Molluscicides, *Encyclopedia of Pest Management*, Ch. 219, p. 506-508, 2002.

Whalon, M., Mota-Sanchez, D., Hollingworth, R., Analysis of Global Pesticide Resistance in Arthropods, *Global Pesticide Resistance in Arthropods*, Ch. 1, p. 5-33, 2008.

Definitions Used in this Disclosure

The examples given in these definitions are generally non-exhaustive and must not be construed as limiting this disclosure. It is understood that a substituent should comply with chemical bonding rules and steric compatibility constraints in relation to the particular molecule to which it is attached. These definitions are only to be used for the purposes of this disclosure.

The phrase "active ingredient" means a material having activity useful in controlling pests, and/or that is useful in helping other materials have better activity in controlling pests, examples of such materials include, but are not limited to, acaricides, algicides, antifeedants, avicides, bactericides, bird repellents, chemosterilants, fungicides, herbicide safeners, herbicides, insect attractants, insect repellents, insecticides, mammal repellents, mating disrupters, molluscicides, nematicides, plant activators, plant growth regulators, rodenticides, synergists, and virucides (see alanwood.net). Specific examples of such materials include, but are not limited to, the materials listed in active ingredient group alpha.

The phrase "active ingredient group alpha" (hereafter "AIGA") means collectively the following materials:

(1) (3-ethoxypropyl)mercury bromide, 1,2-dibromoethane, 1,2-dichloroethane, 1,2-dichloropropane, 1,3-dichloropropene, 1-MCP, 1-methylcyclopropene, 1-naphthol, 2-(octylthio)ethanol, 2,3,3-TPA, 2,3,5-tri-iodobenzoic acid, 2,3,6-TBA, 2,4,5-T, 2,4,5-TB, 2,4,5-TP, 2,4-D, 2,4-DB, 2,4-DEB, 2,4-DEP, 2,4-DES, 2,4-DP, 2,4-MCPA, 2,4-MCPB, 2iP, 2-methoxyethylmercury chloride, 2-phenylphenol, 3,4-DA, 3,4-DB, 3,4-DP, 3,6-dichloropicolinic acid, 4-aminopyridine, 4-CPA, 4-CPB, 4-CPP, 4-hydroxyphenethyl alcohol, 8-hydroxyquinoline sulfate, 8-phenylmercurioxyquinoline, abamectin, abamectin-aminomethyl, abscisic acid, ACC, acephate, acequinocyl, acetamiprid, acethion, acetochlor, acetofenate, acetophos, acetoprole, acibenzolar, acifluorfen, aclonifen, ACN, acrep, acrinathrin, acrolein, acrylonitrile, acynonapyr, acypetacs, afidopyropen, afoxolaner, alachlor, alanap, alanycarb, albendazole, aldicarb, aldicarb sulfone, aldimorph, aldoxycarb, aldrin, allethrin, allicin, allidochlor, allosamidin, alloxydim, allyl alcohol, allyxycarb, alorac, alpha-cypermethrin, alpha-endosulfan, alphamethrin, altretamine, aluminium phosphide, aluminum phosphide, ametoctradin, ametridione, ametryn, ametryne, amibuzin, amicarbazone, amicarthiazol, amidithion, amidoflumet, amidosulfuron, aminocarb, aminocyclopyrachlor, aminopyralid, aminopyrifen, aminotriazole, amiprofos-methyl, amiprophos, amiprophos-methyl, amisulbrom, amiton, amitraz, amitrole, ammonium sulfamate, amobam, amorphous silica gel, amorphous silicon dioxide, ampropylfos, AMS, anabasine, ancymidol, anilazine, anilofos, anisuron, anthraquinone, antu, apholate, aramite, arprocarb, arsenous oxide, asomate, aspirin, asulam, athidathion, atraton, atrazine, aureofungin, avermectin B1, AVG, aviglycine, azaconazole, azadirachtin, azafenidin, azamethiphos, azidithion, azimsulfuron, azinphosethyl, azinphos-ethyl, azinphosmethyl, azinphos-methyl, aziprotryn, aziprotryne, azithiram, azobenzene, azocyclotin, azothoate, azoxystrobin, bachmedesh, barban, barbanate, barium hexafluorosilicate, barium polysulfide, barium silicofluoride, barthrin, basic copper carbonate, basic copper chloride, basic copper sulfate, BCPC, beflubutamid, beflubutamid-M, benalaxyl, benalaxyl-M, benazolin, bencarbazone, benclothiaz, bendaqingbingzhi, bendiocarb, bendioxide, benefin, benfluralin, benfuracarb, benfuresate, benmihuangcaoan, benodanil, benomyl, benoxacor, benoxafos, benquinox, bensulfuron, bensulide, bensultap, bentaluron, bentazon, bentazone, benthiavalicarb, benthiazole, benthiocarb, bentranil, benzadox, benzalkonium chloride, benzamacril, benzamizole, benzamorf, benzene hexachloride, benzfendizone, benzimine, benzipram, benzobicyclon, benzoepin, benzofenap, benzofluor, benzohydroxamic acid, benzomate, benzophosphate, benzothiadiazole, benzovindiflupyr, benzoximate, benzoylprop, benzpyrimoxan, benzthiazuron, benzuocaotong, benzyl benzoate, benzyladenine, berberine, beta-cyfluthrin, beta-cypermethrin, bethoxazin, BHC, bialaphos, bicyclopyrone, bifenazate, bifenox, bifenthrin, bifujunzhi, bilanafos, binapacryl, bingqingxiao, bioallethrin, bioethanomethrin, biopermethrin, bioresmethrin, biphenyl, bisazir, bismerthiazol, bismerthiazol-copper, bisphenylmercury methylenedi(x-naphthalene-y-sulphonate), bispyribac, bistrifluron, bisultap, bitertanol, bithionol, bixafen, bixlozone, blasticidin-S, borax, Bordeaux mixture, boric acid, boscalid, BPPS, brassinolide, brassinolide-ethyl, brevicomin, brodifacoum, brofenprox, brofenvalerate, broflanilide, brofluthrinate, bromacil, bromadiolone, bromchlophos, bromethalin, bromethrin, bromfenvinfos, bromoacetamide, bromobonil, bromobutide, bromociclen, bromocyclen, bromo-DDT, bromofenoxim, bromofos, bromomethane, bromophos, bromophos-ethyl, bromopropylate, bromothalonil, bromoxynil, brompyrazon, bromuconazole, bronopol, BRP, BTH, bucarpolate, bufencarb, buminafos, bupirimate, buprofezin, Burgundy mixture, busulfan, busulphan, butacarb, butachlor, butafenacil, butam, butamifos, butane-fipronil, butathiofos, butenachlor, butene-fipronil, butethrin, buthidazole, buthiobate, buthiuron, butifos, butocarboxim, butonate, butopyronoxyl, butoxycarboxim, butralin, butrizol, butroxydim, buturon, butylamine, butylate, butylchlorophos, butylene-fipronil, cacodylic acid, cadusafos, cafenstrole, calciferol, calcium arsenate, calcium chlorate, calcium cyanamide, calcium cyanide, calcium polysulfide, calvinphos, cambendichlor, camphechlor, camphor, captafol, captan, carbam, carbamorph, carbanolate, carbaril, carbaryl, carbasulam, carbathion, carbendazim, carbendazol, carbetamide, carbofenotion, carbofuran, carbon disulfide, carbon tetrachloride, carbonyl sulfide, carbophenothion, carbophos, carbosulfan, carboxazole, carboxide, carboxin, carfentrazone, carpropamid, cartap, carvacrol, carvone, CAVP, CDAA, CDEA, CDEC, cellocidin, CEPC, ceralure, cerenox, cevadilla, Cheshunt mixture, chinalphos, chinalphos-methyl, chinomethionat, chinomethionate, chiralaxyl, chitosan, chlobenthiazone, chlomethoxyfen, chloralose, chloramben, chloramine phosphorus, chloramphenicol, chloraniformethan, chloranil, chloranocryl, chlorantraniliprole, chlorazifop, chlorazine, chlorbenside, chlorbenzuron, chlorbicyclen, chlorbromuron, chlorbufam, chlordane, chlordecone, chlordimeform, chlorempenthrin, chloretazate, chlorethephon, chlorethoxyfos, chloreturon, chlorfenac, chlorfenapyr, chlorfenazole, chlorfenethol, chlorfenidim, chlorfenprop, chlorfenson, chlorfensulphide, chlorfenvinphos, chlorfenvinphos-methyl, chlorfluazuron, chlorflurazole, chlorflurenol, chlorfluren, chlorflurenol, chloridazon, chlorimuron, chlorinate, chlor-IPC, chlormephos, chlormequat, chlormesulone, chlormethoxynil, chlornidine, chlornitrofen, chloroacetic acid, chlorobenzilate, chlorodinitronaphthalenes, chlorofénizon, chloroform, chloromebuform, chloromethiuron, chloroneb, chlorophacinone, chlorophos, chloropicrin, chloropon, chloroprallethrin, chloropropylate, chlorothalonil, chlorotoluron, chloroxifenidim, chloroxuron, chloroxynil, chlorphonium, chlorphoxim, chlorprazophos, chlorprocarb, chlorpropham, chlorpyrifos, chlorpyrifos-methyl, chlorquinox, chlorsulfuron, chlorthal, chlorthiamid, chlorthiophos, chlortoluron, chlozolinate, chltosan, cholecalciferol, choline chloride, chromafenozide, cicloheximide, cimectacarb, cimetacarb, cinerin I, cinerin II, cinerins, cinidon-ethyl, cinmethylin, cinosulfuron, cintofen, ciobutide, cisanilide, cismethrin, clacyfos, clefoxydim, clenpirin, clenpyrin, clethodim, climbazole, cliodinate, clodinafop, cloethocarb, clofencet, clofenotane, clofentezine, clofenvinfos, clofibric acid, clofop, clomazone, clomeprop, clonitralid, cloprop, cloproxydim, clopyralid, cloquintocet, cloransulam, closantel, clothianidin, clotrimazole, cloxyfonac, cloxylacon, clozylacon, CMA, CMMP, CMP, CMU, codlelure, colecalciferol, colophonate, copper 8-quinolinolate, copper acetate, copper acetoarsenite, copper arsenate, copper carbonate, basic, copper hydroxide, copper naphthenate, copper oleate, copper oxychloride, copper silicate, copper sulfate, copper sulfate, basic, copper zinc chromate, coumachlor, coumafène, coumafos, coumafuryl, coumaphos, coumatetralyl, coumethoxystrobin, coumithoate, coumoxystrobin, CPMC, CPMF, CPPC, credazine, cresol, cresylic acid, crimidine, crotamiton, crotoxyfos, crotoxyphos, crufomate, cryolite, cue-lure, cufraneb, cumyleron, cumyluron, cuprobam, cuprous oxide, curcumenol, CVMP, cyanamide, cyanatryn, cyanazine, cyanofenphos, cyanogen, cyanophos, cyanthoate, cyantraniliprole, cyanuric acid, cyazofamid, cybutryne, cyclafuramid, cyclanilide, cyclaniliprole, cyclethrin, cycloate, cycloheximide, cycloprate, cycloprothrin, cyclopyranil, cyclopyrimorate, cyclosulfamuron, cycloxydim, cycluron, cyenopyrafen, cyflufenamid, cyflumetofen, cyfluthrin, cyhalodiamide, cyhalofop, cyhalothrin, cyhexatin, cymiazole, cymoxanil, cyometrinil, cypendazole, cypermethrin, cyperquat, cyphenothrin, cyprazine, cyprazole, cyproconazole, cyprodinil, cyprofuram, cypromid, cyprosulfamide, cyromazine, cythioate, cytrex, daimuron, dalapon, daminozide, dayoutong, dazomet, DBCP, d-camphor, DCB, DCIP, DCPA (Japan), DCPA (USA), DCPTA, DCU, DDD, DDPP, DDT, DDVP, debacarb, decafentin, decamethrin, decarbofuran, deet, dehydroacetic acid, deiquat, delachlor, delnav, deltamethrin, demephion, demephion-O, demephion-S, demeton, demeton-methyl, demeton-O, demeton-O-methyl, demeton-S, demeton-S-methyl, demeton-S-methyl sulphone, demeton-S-methylsulphon, DEP, depalléthrine, derris, desmedipham, desmetryn, desmetryne, d-fanshiluquebingjuzhi, diafenthiuron, dialifor, dialifos, diallate, di-allate, diamidafos, dianat, diatomaceous earth, diatomite, diazinon, dibrom, dibutyl phthalate, dibutyl succinate, dicamba, dicapthon, dichlobenil, dichlobentiazox, dichlofenthion, dichlofluanid, dichlone, dichloralurea, dichlorbenzuron, dichlorfenidim, dichlorflurecol, dichlorflurenol, dichlormate, dichlormid, dichloromethane, dichlorophen, dichlorprop, dichlorprop-P, dichlorvos, dichlozolin, dichlozoline, diclobutrazol, diclocymet, diclofop, diclomezine, dicloran, dicloromezotiaz, diclosulam, dicofol, dicophane, dicoumarol, dicresyl, dicrotophos, dicryl, dicumarol, dicyclanil, dicyclonon, dieldrin, dienochlor, diethamquat, diethatyl, diethion, diéthion, diethofencarb, dietholate, diéthon, diethyl pyrocarbonate, diethyltoluamide, difenacoum, difenoconazole, difenopenten, difenoxuron, difenzoquat, difethialone, diflovidazin, diflubenzuron, diflufenican, diflufenicanil, diflufenzopyr, diflumetorim, dikegulac, dilor, dimatif, dimefluthrin, dimefox, dimefuron, dimehypo, dimepiperate, dimetachlone, dimetan, dimethacarb, dimethachlone, dimethachlor, dimethametryn, dimethenamid, dimethenamid-P, dimethipin, dimethirimol, dimethoate, dimethomorph, dimethrin, dimethyl carbate, dimethyl disulfide, dimethyl phthalate, dimethylvinphos, dimetilan, dimexano, dimidazon, dimoxystrobin, dimpropyridaz, dimpylate, dimuron, dinex, dingjunezuo, diniconazole, diniconazole-M, dinitramine, dinitrophenols, dinobuton, dinocap, dinocap-4, dinocap-6, dinocton, dinofenate, dinopenton, dinoprop, dinosam, dinoseb, dinosulfon, dinotefuran, dinoterb, dinoterbon, diofenolan, dioxabenzofos, dioxacarb, dioxathion, dioxation, diphacin, diphacinone, diphenadione, diphenamid, diphenamide, diphenyl sulfone, diphenylamine, diphenylsulphide, diprogulic acid, dipropalin, dipropetryn, dipterex, dipymetitrone, dipyrithione, diquat, disodium tetraborate, disosultap, disparlure, disugran, disul, disulfiram, disulfoton, ditalimfos, dithianon, dithicrofos, dithioether, dithiométon, dithiopyr, diuron, dixanthogen, d-limonene, DMDS, DMPA, DNOC, dodemorph, dodicin, dodine, dofenapyn, doguadine, dominicalure, doramectin, DPC, drazoxolon, DSMA, d-trans-allethrin, d-trans-resmethrin, dufulin, dymron, EBEP, EBP, ebufos, ecdysterone, echlomezol, EDB, EDC, EDDP, edifenphos, eglinazine, emamectin, EMPC, empenthrin, enadenine, endosulfan, endothal, endothall, endothion, endrin, enestroburin, enilconazole, enoxastrobin, ephirsulfonate, EPN, epocholeone, epofenonane, epoxiconazole, eprinomectin, epronaz, epsilon-metofluthrin, epsilon-momfluorothrin, EPTC, erbon, ergocalciferol, erlujixiancaoan, esdépalléthrine, esfenvalerate, ESP, esprocarb, etacelasil, etaconazole, etaphos, etem, ethaboxam, ethachlor, ethalfluralin, ethametsulfuron, ethaprochlor, ethephon, ethidimuron, ethiofencarb, ethiolate, ethion, ethiozin, ethiprole, ethirimol, ethoate-methyl, ethobenzanid, ethofumesate, ethohexadiol, ethoprop, ethoprophos, ethoxyfen, ethoxyquin, ethoxysulfuron, ethychlozate, ethyl formate, ethyl pyrophosphate, ethylan, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, ETM, etnipromid, etobenzanid, etofenprox, etoxazole, etridiazole, etrimfos, étrimphos, eugenol, EXD, famoxadone, famphur, fenac, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorphos, fenclofos, fenclorim, fenethacarb, fenfluthrin, fenfuram, fenhexamid, fenidin, fenitropan, fenitrothion, fénizon, fenjuntong, fenobucarb, fenolovo, fenoprop, fenothiocarb, fenoxacrim, fenoxanil, fenoxaprop, fenoxaprop-P, fenoxasulfone, fenoxycarb, fenpiclonil, fenpicoxamid, fenpirithrin, fenpropathrin, fenpropidin, fenpropimorph, fenpyrazamine, fenpyroximate, fenquinotrione, fenridazon, fenson, fensulfothion, fenteracol, fenthiaprop, fenthion, fenthion-ethyl, fentiaprop, fentin, fentrazamide, fentrifanil, fenuron, fenuron-TCA, fenvalerate, ferbam, ferimzone, ferric phosphate, ferrous sulfate, fipronil, flamprop, flamprop-M, flazasulfuron, flocoumafen, flometoquin, flonicamid, florasulam, florpyrauxifen, florylpicoxamid, fluacrypyrim, fluazaindolizine, fluazifop, fluazifop-P, fluazinam, fluazolate, fluazuron, flubendiamide, flubenzimine, flubrocythrinate, flucarbazone, flucetosulfuron, fluchloralin, flucofuron, flucycloxuron, flucythrinate, fludioxonil, fluénéthyl, fluenetil, fluensulfone, flufenacet, flufenerim, flufenican, flufenoxuron, flufenoxystrobin, flufenprox, flufenpyr, flufenzine, flufiprole, fluhexafon, fluindapyr, flumethrin, flumetover, flumetralin, flumetsulam, flumezin, flumiclorac, flumioxazin, flumipropyn, flumorph, fluometuron, fluopicolide, fluopimomide, fluopyram, fluorbenside, fluoridamid, fluoroacetamide, fluoroacetic acid, fluorochloridone, fluorodifen, fluoroglycofen, fluoroimide, fluoromide, fluoromidine, fluoronitrofen, fluoroxypyr, fluothiuron, fluotrimazole, fluoxapiprolin, fluoxastrobin, flupoxam, flupropacil, flupropadine, flupropanate, flupyradifurone, flupyrimin, flupyrsulfuron, fluquinconazole, fluralaner, flurazole, flurecol, flurenol, fluridone, flurochloridone, fluromidine, fluroxypyr, flurprimidol, flursulamid, flurtamone, flusilazole, flusulfamide, flutenzine, fluthiacet, fluthiamide, flutianil, flutolanil, flutriafol, fluvalinate, fluxametamide, fluxapyroxad, fluxofenim, folpel, folpet, fomesafen, fonofos, foramsulfuron, forchlorfenuron, formaldehyde, formetanate, formothion, formparanate, fosamine, fosetyl, fosmethilan, fospirate, fosthiazate, fosthietan, frontalin, fthalide, fuberidazole, fucaojing, fucaomi, fujunmanzhi, fulumi, fumarin, funaihecaoling, fuphenthiourea, furalane, furalaxyl, furamethrin, furametpyr, furan tebufenozide, furathiocarb, furcarbanil, furconazole, furconazole-cis, furethrin, furfural, furilazole, furmecyclox, furophanate, furyloxyfen, gamma-BHC, gamma-cyhalothrin, gamma-HCH, genit, gibberellic acid, gibberellin A3, gibberellins, gliftor, glitor, glucochloralose, glufosinate, glufosinate-P, glyodin, glyoxime, glyphosate, glyphosine, gossyplure, grandlure, griseofulvin, guanoctine, guazatine, halacrinate, halauxifen, halfenprox, halofenozide, halosafen, halosulfuron, haloxydine, haloxyfop, haloxyfop-P, haloxyfop-R, HCA, HCB, HCH, hemel, hempa, HEOD, heptachlor, heptafluthrin, heptenophos, heptopargil, herbimycin, herbimycin A, heterophos, hexachlor, hexachloran, hexachloroacetone, hexachlorobenzene, hexachlorobutadiene, hexachlorophene, hexaconazole, hexaflumuron, hexafluoramin, hexaflurate, hexalure, hexamide, hexazinone, hexylthiofos, hexythiazox, HHDN, holosulf, homobrassinolide, huancaiwo, huanchongjing, huangcaoling, huanjunzuo, hydramethylnon, hydrargaphen, hydrated lime, hydrogen cyanamide, hydrogen cyanide, hydroprene, hydroxyisoxazole, hymexazol, hyquincarb, IAA, IBA, IBP, icaridin, imazalil, imazamethabenz, imazamox, imazapic, imazapyr, imazaquin, imazethapyr, imazosulfuron, imibenconazole, imicyafos, imidacloprid, imidaclothiz, iminoctadine, imiprothrin, inabenfide, indanofan, indaziflam, indoxacarb, inezin, infusorial earth, inpyrfluxam, iodobonil, iodocarb, iodofenphos, iodomethane, iodosulfuron, iofensulfuron, ioxynil, ipazine, IPC, ipconazole, ipfencarbazone, ipfentrifluconazole, ipflufenoquin, iprobenfos, iprodione, iprovalicarb, iprymidam, ipsdienol, ipsenol, IPSP, IPX, isamidofos, isazofos, isobenzan, isocarbamid, isocarbamide, isocarbophos, isocil, isocycloseram, isodrin, isofenphos, isofenphos-methyl, isofetamid, isoflucypram, isolan, isomethiozin, isonoruron, isopamphos, isopolinate, isoprocarb, isoprocil, isopropalin, isopropazol, isoprothiolane, isoproturon, isopyrazam, isopyrimol, isothioate, isotianil, isouron, isovaledione, isoxaben, isoxachlortole, isoxadifen, isoxaflutole, isoxapyrifop, isoxathion, isuron, ivermectin, ixoxaben, izopamfos, izopamphos, japonilure, japothrins, jasmolin I, jasmolin II, jasmonic acid, jiahuangchongzong, jiajizengxiaolin, jiaxiangjunzhi, jiecaowan, jiecaoxi, Jinganmycin A, jodfenphos, juvenile hormone I, juvenile hormone II, juvenile hormone III, kadethrin, kappa-bifenthrin, kappa-tefluthrin, karbutilate, karetazan, kasugamycin, kejunlin, kelevan, ketospiradox, kieselguhr, kinetin, kinoprene, kiralaxyl, kresoxim-methyl, kuicaoxi, lactofen, lambda-cyhalothrin, lancotrione, latilure, lead arsenate, lenacil, lepimectin, leptophos, lianbenjingzhi, lime sulfur, lindane, lineatin, linuron, lirimfos, litlure, looplure, lotilaner, lufenuron, lüfuqingchongxianan, lüxiancaolin, lvdingjunzhi, lvfumijvzhi, lvxiancaolin, lythidathion, M-74, M-81, MAA, magnesium phosphide, malathion, maldison, maleic hydrazide, malonoben, maltodextrin, MAMA, mancopper, mancozeb, mandestrobin, mandipropamid, maneb, matrine, mazidox, MCC, MCP, MCPA, MCPA-thioethyl, MCPB, MCPP, mebenil, mecarbam, mecarbinzid, mecarphon, mecoprop, mecoprop-P, medimeform, medinoterb, medlure, mefenacet, mefenoxam, mefenpyr, mefentrifluconazole, mefluidide, megatomoic acid, melissyl alcohol, melitoxin, MEMC, menazon, MEP, mepanipyrim, meperfluthrin, mephenate, mephosfolan, mepiquat, mepronil, meptyldinocap, mercaptodimethur, mercaptophos, mercaptophos thiol, mercaptothion, mercuric chloride, mercuric oxide, mercurous chloride, merphos, merphos oxide, mesoprazine, mesosulfuron, mesotrione, mesulfen, mesulfenfos, mesulphen, metacresol, metaflumizone, metalaxyl, metalaxyl-M, metaldehyde, metam, metamifop, metamitron, metaphos, metaxon, metazachlor, metazosulfuron, metazoxolon, metcamifen, metconazole, metepa, metflurazon, methabenzthiazuron, methacrifos, methalpropalin, metham, methamidophos, methasulfocarb, methazole, methfuroxam, methibenzuron, methidathion, methiobencarb, methiocarb, methiopyrisulfuron, methiotepa, methiozolin, methiuron, methocrotophos, métholcarb, methometon, methomyl, methoprene, methoprotryn, methoprotryne, methoquin-butyl, methothrin, methoxychlor, methoxyfenozide, methoxyphenone, methyl apholate, methyl bromide, methyl eugenol, methyl iodide, methyl isothiocyanate, methyl parathion, methylacetophos, methylchloroform, methyldithiocarbamic acid, methyldymron, methylene chloride, methyl-isofenphos, methylmercaptophos, methylmercaptophos oxide, methylmercaptophos thiol, methylmercury benzoate, methylmercury dicyandiamide, methylmercury pentachlorophenoxide, methylneodecanamide, methylnitrophos, methyltriazothion, metiozolin, metiram, metiram-zinc, metobenzuron, metobromuron, metofluthrin, metolachlor, metolcarb, metometron, metominostrobin, metosulam, metoxadiazone, metoxuron, metrafenone, metriam, metribuzin, metrifonate, metriphonate, metsulfovax, metsulfuron, metyltetraprole, mevinphos, mexacarbate, miechuwei, mieshuan, miewenjuzhi, milbemectin, milbemycin oxime, milneb, mimanan, mipafox, MIPC, mirex, MNAF, moguchun, molinate, molosultap, momfluorothrin, monalide, monisuron, monoamitraz, monochloroacetic acid, monocrotophos, monolinuron, monomehypo, monosulfiram, monosulfuron, monosultap, monuron, monuron-TCA, morfamquat, moroxydine, morphothion, morzid, moxidectin, MPMC, MSMA, MTMC, muscalure, myclobutanil, myclozolin, myricyl alcohol, N-(ethylmercury)-p-toluenesulphonanilide, NAA, NAAm, nabam, naftalofos, naled, naphthalene, naphthaleneacetamide, naphthalic anhydride, naphthalophos, naphthoxyacetic acids, naphthylacetic acids, naphthylindane-1,3-diones, naphthyloxyacetic acids, naproanilide, napropamide, napropamide-M, naptalam, natamycin, NBPOS, neburea, neburon, nendrin, neonicotine, nichlorfos, niclofen, niclosamide, nicobifen, nicosulfuron, nicotine, nicotine sulfate, nifluridide, nikkomycins, NIP, nipyraclofen, nipyralofen, nitenpyram, nithiazine, nitralin, nitrapyrin, nitrilacarb, nitrofen, nitrofluorfen, nitrostyrene, nitrothal-isopropyl, nobormide, nonanol, norbormide, norea, norflurazon, nornicotine, noruron, novaluron, noviflumuron, NPA, nuarimol, nuranone, OCH, octachlorodipropyl ether, octhilinone, o-dichlorobenzene, ofurace, omethoate, o-phenylphenol, orbencarb, orfralure, orthobencarb, ortho-dichlorobenzene, orthosulfamuron, oryctalure, orysastrobin, oryzalin, osthol, osthole, ostramone, ovatron, ovex, oxabetrinil, oxadiargyl, oxadiazon, oxadixyl, oxamate, oxamyl, oxapyrazon, oxapyrazone, oxasulfuron, oxathiapiprolin, oxaziclomefone, oxazosulfyl, oxine-copper, oxine-Cu, oxolinic acid, oxpoconazole, oxycarboxin, oxydemeton-methyl, oxydeprofos, oxydisulfoton, oxyenadenine, oxyfluorfen, oxymatrine, oxytetracycline, oxythioquinox, PAC, paclobutrazol, paichongding, palléthrine, PAP, para-dichlorobenzene, parafluron, paraquat, parathion, parathion-methyl, parinol, Paris green, PCNB, PCP, PCP-Na, p-dichlorobenzene, PDJ, pebulate, pédinex, pefurazoate, pelargonic acid, penconazole, pencycuron, pendimethalin, penfenate, penflufen, penfluron, penoxalin, penoxsulam, pentachlorophenol, pentachlorophenyl laurate, pentanochlor, penthiopyrad, pentmethrin, pentoxazone, perchlordecone, perfluidone, permethrin, pethoxamid, PHC, phenamacril, phenamacril-ethyl, phénaminosulf, phenazine oxide, phénétacarbe, phenisopham, phenkapton, phenmedipham, phenmedipham-ethyl, phenobenzuron, phenothiol, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosametine, phosazetim, phosazetin, phoscyclotin, phosdiphen, phosethyl, phosfolan, phosfolan-methyl, phosglycin, phosmet, phosnichlor, phosphamide, phosphamidon, phosphine, phosphinothricin, phosphocarb, phosphorus, phostin, phoxim, phoxim-methyl, phthalide, phthalophos, phthalthrin, picarbutrazox, picaridin, picloram, picolinafen, picoxystrobin, pimaricin, pindone, pinoxaden, piperalin, piperazine, piperonyl butoxide, piperonyl cyclonene, piperophos, piproctanly, piproctanyl, piprotal, pirimetaphos, pirimicarb, piriminil, pirimioxyphos, pirimiphos-ethyl, pirimiphos-methyl, pival, pivaldione, plifenate, PMA, PMP, polybutenes, polycarbamate, polychlorcamphene, polyethoxyquinoline, polyoxin D, polyoxins, polyoxorim, polythialan, potassium arsenite, potassium azide, potassium cyanate, potassium ethylxanthate, potassium naphthenate, potassium polysulfide, potassium thiocyanate, pp'-DDT, prallethrin, precocene I, precocene II, precocene III, pretilachlor, primidophos, primisulfuron, probenazole, prochloraz, proclonol, procyazine, procymidone, prodiamine, profenofos, profluazol, profluralin, profluthrin, profoxydim, profurite-aminium, proglinazine, prohexadione, prohydrojasmon, promacyl, promecarb, prometon, prometryn, prometryne, promurit, pronamide, pronitridine, propachlor, propafos, propamidine, propamocarb, propanil, propaphos, propaquizafop, propargite, proparthrin, propazine, propetamphos, propham, propiconazole, propidine, propineb, propisochlor, propoxur, propoxycarbazone, propyl isome, propyrisulfuron, propyzamide, proquinazid, prosuler, prosulfalin, prosulfocarb, prosulfuron, prothidathion, prothiocarb, prothioconazole, prothiofos, prothoate, protrifenbute, proxan, prymidophos, prynachlor, psoralen, psoralene, pydanon, pydiflumetofen, pyflubumide, pymetrozine, pyracarbolid, pyraclofos, pyraclonil, pyraclostrobin, pyraflufen, pyrafluprole, pyramat, pyrametostrobin, pyraoxystrobin, pyrapropoyne, pyrasulfotole, pyraziflumid, pyrazolate, pyrazolynate, pyrazon, pyrazophos, pyrazosulfuron, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridachlometyl, pyridafol, pyridalyl, pyridaphenthion, pyridaphenthione, pyridate, pyridinitril, pyrifenox, pyrifluquinazon, pyriftalid, pyrimétaphos, pyrimethanil, pyrimicarbe, pyrimidifen, pyriminobac, pyriminostrobin, pyrimiphos-ethyl, pyrimiphos-methyl, pyrimisulfan, pyrimitate, pyrinuron, pyriofenone, pyriprole, pyripropanol, pyriproxyfen, pyrisoxazole, pyrithiobac, pyrolan, pyroquilon, pyroxasulfone, pyroxsulam, pyroxychlor, pyroxyfur, qincaosuan, qingkuling, quassia, quinacetol, quinalphos, quinalphos-methyl, quinazamid, quinclorac, quinconazole, quinmerac, quinoclamine, quinofumelin, quinomethionate, quinonamid, quinothion, quinoxyfen, quintiofos, quintozene, quizalofop, quizalofop-P, quwenzhi, quyingding, rabenzazole, rafoxanide, R-diniconazole, rebemide, reglone, renriduron, rescalure, resmethrin, rhodethanil, rhodojaponin-III, ribavirin, rimsulfuron, rizaole, R-metalaxyl, rodéthanil, ronnel, rotenone, ryania, sabadilla, saflufenacil, saijunmao, saisentong, salicylanilide, salifluofen, sanguinarine, santonin, S-bioallethrin, schradan, scilliroside, sebuthylazine, secbumeton, sedaxane, selamectin, semiam-itraz, sesamex, sesamolin, sesone, sethoxydim, sevin, shuangjiaancaolin, shuangjianancaolin, S-hydroprene, siduron, sifumijvzhi, siglure, silafluofen, silatrane, silica aerogel, silica gel, silthiofam, silthiopham, silthiophan, silvex, simazine, simeconazole, simeton, simetryn, simetryne, sintofen, S-kinoprene, slaked lime, SMA, S-methoprene, S-metolachlor, sodium arsenite, sodium azide, sodium chlorate, sodium cyanide, sodium fluoride, sodium fluoroacetate, sodium hexafluorosilicate, sodium naphthenate, sodium o-phenylphenoxide, sodium orthophenylphenoxide, sodium pentachlorophenate, sodium pentachlorophenoxide, sodium polysulfide, sodium silicofluoride, sodium tetrathiocarbonate, sodium thiocyanate, solan, sophamide, spinetoram, spinosad, spirodiclofen, spiromesifen, spiropidion, spirotetramat, spiroxamine, stirofos, streptomycin, strychnine, sulcatol, sulcofuron, sulcotrione, sulfallate, sulfentrazone, sulfiram, sulfluramid, sulfodiazole, sulfometuron, sulfosate, sulfosulfuron, sulfotep, sulfotepp, sulfoxaflor, sulfoxide, sulfoxime, sulfur, sulfuric acid, sulfuryl fluoride, sulglycapin, sulphosate, sulprofos, sultropen, swep, tau-fluvalinate, tavron, tazimcarb, TBTO, TBZ, TCA, TCBA, TCMTB, TCNB, TDE, tebuconazole, tebufenozide, tebufenpyrad, tebufloquin, tebupirimfos, tebutam, tebuthiuron, tecloftalam, tecnazene, tecoram, tedion, teflubenzuron, tefluthrin, tefuryltrione, tembotrione, temefos, temephos, tepa, TEPP, tepraloxydim, teproloxydim, terallethrin, terbacil, terbucarb, terbuchlor, terbufos, terbumeton, terbuthylazine, terbutol, terbutryn, terbutryne, terraclor, terramicin, terramycin, tetcyclacis, tetflupyrolimet, tetrachlorantraniliprole, tetrachloroethane, tetrachlorvinphos, tetraconazole, tetradifon, tetradisul, tetrafluron, tetramethrin, tetramethylfluthrin, tetramine, tetranactin, tetraniliprole, tetrapion, tetrasul, thallium sulfate, thallous sulfate, thenylchlor, theta-cypermethrin, thiabendazole, thiacloprid, thiadiazine, thiadifluor, thiamethoxam, thiameturon, thiapronil, thiazafluron, thiazfluron, thiazone, thiazopyr, thicrofos, thicyofen, thidiazimin, thidiazuron, thiencarbazone, thifensulfuron, thifluzamide, thimerosal, thimet, thiobencarb, thiocarboxime, thiochlorfenphim, thiochlorphenphime, thiocyanatodinitrobenzenes, thiocyclam, thiodan, thiodiazole-copper, thiodicarb, thiofanocarb, thiofanox, thiofluoximate, thiohempa, thiomersal, thiometon, thionazin, thiophanate, thiophanate-ethyl, thiophanate-methyl, thiophos, thioquinox, thiosemicarbazide, thiosultap, thiotepa, thioxamyl, thiram, thiuram, thuringiensin, tiabendazole, tiadinil, tiafenacil, tiaojiean, TIBA, tifatol, tiocarbazil, tioclorim, tioxazafen, tioxymid, tirpate, TMTD, tolclofos-methyl, tolfenpyrad, tolprocarb, tolpyralate, tolyfluanid, tolylfluanid, tolylmercury acetate, tomarin, topramezone, toxaphene, TPN, tralkoxydim, tralocythrin, tralomethrin, tralopyril, transfluthrin, transpermethrin, tretamine, triacontanol, triadimefon, triadimenol, triafamone, triallate, tri-allate, triamiphos, triapenthenol, triarathene, triarimol, triasulfuron, triazamate, triazbutil, triaziflam, triazophos, triazothion, triazoxide, tribasic copper chloride, tribasic copper sulfate, tribenuron, tribufos, tributyltin oxide, tricamba, trichlamide, trichlopyr, trichlorfon, trichlormetaphos-3, trichloronat, trichloronate, trichlorotrinitrobenzenes, trichlorphon, triclopyr, triclopyricarb, tricresol, tricyclazole, tricyclohexyltin hydroxide, tridemorph, tridiphane, trietazine, trifenmorph, trifenofos, trifloxystrobin, trifloxysulfuron, trifludimoxazin, triflumezopyrim, triflumizole, triflumuron, trifluralin, triflusulfuron, trifop, trifopsime, triforine, trihydroxytriazine, trimedlure, trimethacarb, trimeturon, trinexapac, triphenyltin, triprene, tripropindan, triptolide, tritac, trithialan, triticonazole, tritosulfuron, truncall, tuoyelin, tyclopyrazoflor, uniconazole, uniconazole-P, urbacide, uredepa, valerate, validamycin, validamycin A, valifenalate, valone, vamidothion, vangard, vaniliprole, vernolate, vinclozolin, vitamin D3, warfarin, xiaochongliulin, xinjunan, xiwojunan, xiwojunzhi, XMC, xylachlor, xylenols, xylylcarb, xymiazole, yishijing, zarilamid, zeatin, zengxiaoan, zengxiaolin, zeta-cypermethrin, zinc naphthenate, zinc phosphide, zinc thiazole, zinc thiozole, zinc trichlorophenate, zinc trichlorophenoxide, zineb, ziram, zolaprofos, zoocoumarin, zoxamide, zuoanjunzhi, zuocaoan, zuojunzhi, zuomihuanglong, α-chlorohydrin, α-ecdysone, α-multistriatin, α-naphthaleneacetic acids, and β-ecdysone;
(2) the following molecules in Table 1

Additionally, another particularly preferred selection of active ingredients are acequinocyl, acetamiprid, acetoprole, avermectin, azinphos-methyl, bifenazate, bifenthrin, carbaryl, carbofuran, chlorfenapyr, chlorfluazuron, chromafenozide, clothianidin, cyfluthrin, cypermethrin, deltamethrin, diafenthiuron, emamectin benzoate, endosulfan, esfenvalerate, ethiprole, etoxazole, fipronil, flonicamid, fluacrypyrim, gamma-cyhalothrin, halofenozide, indoxacarb, lambda-cyhalothrin, lufenuron, malathion, methomyl, novaluron, permethrin, pyridalyl, pyrimidifen, spirodiclofen, tebufenozide,

TABLE 1

Structure of M# - active ingredients

| M# | Structure |
|---|---|
| M1 | 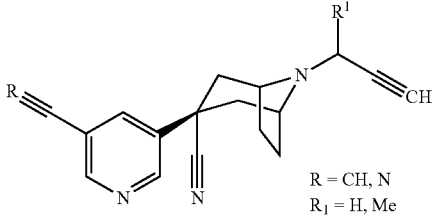 R = CH, N<br>$R_1$ = H, Me |
| M2 | 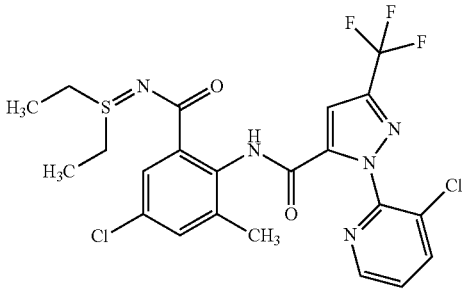 [SMILES: CCS(CC)=NC(=O)c1cc(Cl)cc(C)c1NC(=O)c1cc(C(F)(F)F)nn1-c1ncccc1Cl] |
| M3 | 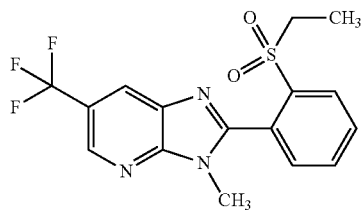 [SMILES: CCS(=O)(=O)c1ccccc1-c1nc2cc(C(F)(F)F)cnc2n1C] |
| M4 | 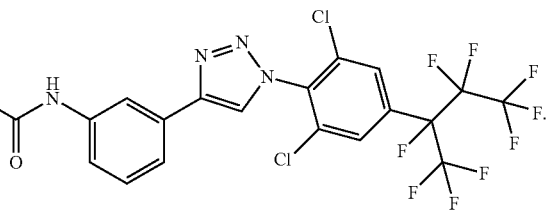 |

As used in this disclosure, each of the above is an active ingredient. For more information consult the materials listed in the "Compendium of Pesticide Common Names," located at Alanwood.net, and various editions, including the on-line edition, of "The Pesticide Manual" located at bcpcdata.com.

A particularly preferred selection of active ingredients are 1,3-dichloropropene, chlorantraniliprole, chlorpyrifos, cyantraniliprole, hexaflumuron, methomyl, methoxyfenozide, noviflumuron, oxamyl, spinetoram, spinosad, sulfoxaflor, and triflumezopyrim (hereafter "AIGA-2").

thiacloprid, thiamethoxam, thiodicarb, tolfenpyrad, and zeta-cypermethrin (hereafter "AIGA-3").

The term "biopesticide" means a microbial biological pest control agent that, in general, is applied in a similar manner to chemical pesticides. Commonly they are bacterial, but there are also examples of fungal control agents, including *Trichoderma* spp. and *Ampelomyces quisqualis*. One well-known biopesticide example is *Bacillus* species, a bacterial disease of Lepidoptera, Coleoptera, and Diptera. Biopesticides include products based on entomopathogenic fungi (e.g. *Metarhizium anisopliae*), entomopathogenic nematodes (e.g. *Steinernema feltiae*), and entomopathogenic viruses (e.g. *Cydia pomonella* granulovirus). Other examples of entomopathogenic organisms include, but are not limited to, baculoviruses, protozoa, and Microsporidia. For the avoidance of doubt, biopesticides are active ingredients.

The term "locus" means a habitat, breeding ground, plant, seed, soil, material, or environment, in which a pest is growing, may grow, or may traverse. For example, a locus may be: where crops, trees, fruits, cereals, fodder species, vines, turf, and/or ornamental plants, are growing; where domesticated animals are residing; the interior or exterior surfaces of buildings (such as places where grains are stored); the materials of construction used in buildings (such as impregnated wood); and the soil around buildings.

The phrase "MoA Material" means an active ingredient having a mode of action ("MoA") as indicated in IRAC MoA Classification v. 8.3, located at irac-online.org., which describes the following groups.

(1) Acetylcholinesterase (AChE) inhibitors, includes the following active ingredients Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, Xylylcarb, Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Isofenphos, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phosalone, Phorate, Phosmet, Phosphamidon, Phoxim, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Trichlorfon, Vamidothion, Pirimiphos-methyl, Imicyafos, and Isopropyl O-(methoxyaminothio-phosphoryl) salicylate.

(2) GABA-gated chloride channel antagonists, includes the following active ingredients Chlordane, Endosulfan, Ethiprole, and Fipronil.

(3) Sodium channel modulators, includes the following active ingredients Acrinathrin, Allethrin, d-cis-trans Allethrin, d-trans Allethrin, Bifenthrin, Bioallethrin, Bioallethrin S-cyclopentenyl, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans-isomers], Deltamethrin, Empenthrin [(EZ)-(1R)-isomers], Esfenvalerate, Etofenprox, Fenpropathrin, Fenvalerate, Flucythrinate, Flumethrin, tau-Fluvalinate, Kadethrin, Pyrethrins (pyrethrum), Halfenprox, Phenothrin [(1R)-trans-isomer], Prallethrin, Resmethrin, Silafluofen, Tefluthrin, Tetramethrin, Tetramethrin [(1R)-isomers], Tralomethrin, Transfluthrin, Permethrin, DDT, and Methoxychlor.

(4) Nicotinic acetylcholine receptor (nAChR) agonists, includes the following active ingredients
(4A) Acetamiprid, Clothianidin, Dinotefuran, Imidacloprid, Nitenpyram, Thiacloprid, Thiamethoxam
(4B) Nicotine,
(4C) Sulfoxaflor,
(4D) Flupyradifurone, and
(4E) Triflumezopyrim.

(5) Nicotinic acetylcholine receptor (nAChR) allosteric activators, includes the following active ingredients Spinetoram and Spinosad.

(6) Chloride channel activators, includes the following active ingredients Abamectin, Emamectin benzoate, Lepimectin, and Milbemectin.

(7) Juvenile hormone mimics, includes the following active ingredients Hydroprene, Kinoprene, Methoprene, Fenoxycarb, and Pyriproxyfen.

(8) Miscellaneous nonspecific (multi-site) inhibitors, includes the following active ingredients Methyl Bromide, Chloropicrin, Cryolite, Sulfuryl fluoride, Borax, Boric acid, Disodium octaborate, Sodium borate, Sodium metaborate, Tartar emetic, Diazomet, and Metam.

(9) Chordotonal organ TRPV channel modulators, includes the following active ingredients Afidopyropen, Pymetrozine and Pyrifluquinazon.

(10) Mite growth inhibitors, includes the following active ingredients Clofentezine, Hexythiazox, Diflovidazin, and Etoxazole.

(11) Microbial disruptors of insect midgut membranes, includes the following active ingredients *B.t.* var. *israelensis, B.t.* var. *aizawai, B.t.* var. *kurstaki, B.t.* var. *tenebrionenis,* and *Bacillus sphaericus.*

(12) Inhibitors of mitochondrial ATP synthase, includes the following active ingredients Tetradifon, Propargite, Azocyclotin, Cyhexatin, Fenbutatin oxide, and Diafenthiuron.

(13) Uncouplers of oxidative phosphorylation via disruption of the proton gradient, includes the following active ingredients Chlorfenapyr, DNOC, and Sulfluramid.

(14) Nicotinic acetylcholine receptor (nAChR) channel blockers, includes the following active ingredients Bensultap, Cartap hydrochloride, Thiocyclam, and Thiosultap-sodium.

(15) Inhibitors of chitin biosynthesis, type 0, includes the following active ingredients Bistrifluron, Chlorfluazuron, Diflubenzuron, Flucycloxuron, Flufenoxuron, Hexaflumuron, Lufenuron, Novaluron, Noviflumuron, Teflubenzuron, and Triflumuron.

(16) Inhibitors of chitin biosynthesis, type 1, includes the following active ingredient Buprofezin.

(17) Moulting disruptor, Dipteran, includes the following active ingredient Cyromazine.

(18) Ecdysone receptor agonists, includes the following active ingredients Chromafenozide, Halofenozide, Methoxyfenozide, and Tebufenozide.

(19) Octopamine receptor agonists, includes the following active ingredient Amitraz.

(20) Mitochondrial complex III electron transport inhibitors, includes the following active ingredients Hydramethylnon, Acequinocyl, Bifenazate and Fluacrypyrim.

(21) Mitochondrial complex I electron transport inhibitors, includes the following active ingredients Fenazaquin, Fenpyroximate, Pyrimidifen, Pyridaben, Tebufenpyrad, Tolfenpyrad, and Rotenone.

(22) Voltage-dependent sodium channel blockers, includes the following active ingredients Indoxacarb and Metaflumizone.

(23) Inhibitors of acetyl CoA carboxylase, includes the following active ingredients Spirodiclofen, Spiromesifen, and Spirotetramat.

(24) Mitochondrial complex IV electron transport inhibitors, includes the following active ingredients, Aluminium phosphide, Calcium phosphide, Phosphine, Zinc phosphide, and Cyanide.

(25) Mitochondrial complex II electron transport inhibitors, includes the following active ingredients Cyenopyrafen, Cyflumetofen, and Pyflubumide.

(28) Ryanodine receptor modulators, includes the following active ingredients Chlorantraniliprole, Cyantraniliprole, and Flubendiamide.

(29) Chordotonal Organ Modulators—undefined target site, includes the following active ingredient Flonicamid.

Groups 26 and 27 are unassigned in this version of the classification scheme. Additionally, there is a Group UN that contains active ingredients of unknown or uncertain mode of action. This group includes the following active ingredients, Azadirachtin, Benzoximate, Bromopropylate, Chinomethionat, Dicofol, GS-omega/kappa HXTX-Hv1a peptide, Lime Sulfur, Pyridalyl, and Sulfur.

The term "pest" means an organism that is detrimental to humans, or human concerns (such as, crops, food, livestock, etc.), where said organism is from Phyla Arthropoda, Mollusca, or Nematoda. Particular examples are ants, aphids, bed bugs, beetles, bristletails, caterpillars, cockroaches, crickets, earwigs, fleas, flies, grasshoppers, grubs, hornets, jassids, leafhoppers, lice, locusts, maggots, mealybugs, mites, moths, nematodes, plantbugs, planthoppers, psyllids, sawflies, scales, silverfish, slugs, snails, spiders, springtails, stink bugs, symphylans, termites, *thrips*, ticks, wasps, whiteflies, and wireworms.

Additional examples are pests in
(1) Subphyla Chelicerata, Myriapoda, and Hexapoda.
(2) Classes of Arachnida, Symphyla, and Insecta.
(3) Order Anoplura. A non-exhaustive list of particular genera includes, but is not limited to, *Haematopinus* spp., *Hoplopleura* spp., *Linognathus* spp., *Pediculus* spp., *Polyplax* spp., *Solenopotes* spp., and *Neohaematopinis* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

(4) Order Coleoptera. A non-exhaustive list of particular genera includes, but is not limited to, *Acanthoscelides* spp., *Agriotes* spp., *Anthonomus* spp., *Apion* spp., *Apogonia* spp., *Araecerus* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Dinoderus* spp., *Gnathocerus* spp., *Hemicoelus* spp., *Heterobostruchus* spp., *Hypera* spp., *Ips* spp., *Lyctus* spp., *Megascelis* spp., *Meligethes* spp., *Mezium* spp., *Niptus* spp., *Otiorhynchus* spp., *Pantomorus* spp., *Phyllophaga* spp., *Phyllotreta* spp., *Ptinus* spp., *Rhizotrogus* spp., *Rhynchites* spp., *Rhynchophorus* spp., *Scolytus* spp., *Sphenophorus* spp., *Sitophilus* spp., *Tenebrio* spp., and *Tribolium* spp. A non-exhaustive list of particular species includes, but is not limited to, *Acanthoscelides obtectus, Agrilus planipennis, Ahasverus advena, Alphitobius diaperinus, Anoplophora glabripennis, Anthonomus grandis, Anthrenus verbasci, Anthrenus falvipes, Ataenius spretulus, Atomaria linearis, Attagenus unicolor, Bothynoderes punctiventris, Bruchus pisorum, Callosobruchus maculatus, Carpophilus hemipterus, Cassida vittata, Cathartus quadricollis, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Euvrilletta peltata, Faustinus cubae, Hylobius pales, Hylotrupes bajulus, Hypera postica, Hypothenemus hampei, Lasioderma serricorne, Leptinotarsa decemlineata, Limonius canus, Liogenys fuscus, Liogenys suturalis, Lissorhoptrus oryzophilus, Lophocateres pusillus, Lyctus planicollis, Maecolaspis joliveti, Melanotus communis, Meligethes aeneus, Melolontha melolontha, Necrobia rufipes, Oberea brevis, Oberea linearis, Oryctes rhinoceros, Oryzaephilus mercator, Oryzaephilus surinamensis, Oulema melanopus, Oulema oryzae, Phyllophaga cuyabana, Polycaon stoutti, Popillia japonica, Prostephanus truncatus, Rhyzopertha dominica, Sitona lineatus, Sitophilus granarius, Sitophilus oryzae, Sitophilus zeamais, Stegobium paniceum, Tenebroides mauritanicus, Tribolium castaneum, Tribolium confusum, Trogoderma granarium, Trogoderma variabile, Xestobium rufovillosum*, and *Zabrus tenebrioides*.

(5) Order Dermaptera. A non-exhaustive list of particular species includes, but is not limited to, *Fofficula auricularia*.

(6) Order Blattaria. A non-exhaustive list of particular species includes, but is not limited to, *Blattella germanica, Blattella asahinai, Blatta orientalis, Blatta lateralis, Parcoblatta pennsylvanica, Periplaneta americana, Periplaneta australasiae, Periplaneta brunnea, Periplaneta fuliginosa, Pycnoscelus surinamensis*, and *Supella longipalpa*.

(7) Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Culicoides* spp., *Dasineura* spp., *Delia* spp., *Drosophila* spp., *Fannia* spp., *Hylemya* spp., *Liriomyza* spp., *Musca* spp., *Phorbia* spp., *Pollenia* spp., *Psychoda* spp., *Simulium* spp., *Tabanus* spp., and *Tipula* spp. A non-exhaustive list of particular species includes, but is not limited to, *Agromyza frontella, Anastrepha suspensa, Anastrepha ludens, Anastrepha obliqua, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Liriomyza sativa, Melophagus ovinus, Musca autumnalis, Musca domestica, Oestrus ovis, Oscinella frit, Pegomya betae, Piophila casei, Psila rosae, Rhagoletis cerasi, Rhagoletis pomonella, Rhagoletis mendax, Sitodiplosis mosellana*, and *Stomoxys calcitrans*.

(8) Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Euschistus* spp., *Lepidosaphes* spp., *Lagynotomus* spp., *Lygus* spp., *Macrosiphum* spp., *Nephotettix* spp., *Nezara* spp., *Nilaparvata* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp., and *Unaspis* spp. A non-exhaustive list of particular species includes, but is not limited to, *Acrosternum hilare, Acyrthosiphon pisum, Aleyrodes protella, Aleurodicus dispersus, Aleurothrixus floccosus, Amrasca biguttula biguttula, Aonidiella aurantii, Aphis fabae, Aphis gossypii, Aphis glycines, Aphis pomi, Aulacorthum solani, Bactericera cockerelli, Bagrada hilaris, Bemisia argentifolii, Bemisia tabaci, Blissus leucopterus, Boisea trivittata, Brachycorynella asparagi, Brevennia rehi, Brevicoryne brassicae, Cacopsylla pyri, Cacopsylla pyricola, Calocoris norvegicus, Ceroplastes rubens, Cimex hemipterus, Cimex lectularius, Coccus pseudomagnoliarum, Dagbertus fasciatus, Dichelops furcatus, Diuraphis noxia, Diaphorina citri, Dysaphis plantaginea, Dysdercus suturel-*

*lus, Edessa meditabunda, Empoasca vitis, Eriosoma lanigerum, Erythroneura elegantula, Eurygaster maura, Euschistus conspersus, Euschistus heros, Euschistus servus, Halyomorpha halys, Helopeltis antonii, Hyalopterus pruni, Helopeltis antonii, Helopeltis theivora, Icerya purchasi, Idioscopus nitidulus, Jacobiasca formosana, Laodelphax striatellus, Lecanium corni, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Megacopta cribraria, Metopolophium dirhodum, Mictis longicornis, Myzus persicae, Nasonovia ribisnigri, Nephotettix cincticeps, Neurocolpus longirostris, Nezara viridula, Nilaparvata lugens, Paracoccus marginatus, Paratrioza cockerelli, Parlatoria pergandii, Parlatoria ziziphi, Peregrinus maidis, Phylloxera vitifoliae, Physokermes piceae, Phytocoris califomicus, Phytocoris relativus, Piezodorus guildinii, Planococcus citri, Planococcus ficus, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

(9) Order Hymenoptera. A non-exhaustive list of particular genera includes, but is not limited to, *Acromyrmex* spp., *Atta* spp., *Camponotus* spp., *Diprion* spp., *Dolichovespula* spp., *Formica* spp., *Monomorium* spp., *Neodiprion* spp., *Paratrechina* spp., *Pheidole* spp., *Pogonomyrmex* spp., *Polistes* spp., *Solenopsis* spp., *Technomyrmex,* spp., *Tetramorium* spp., *Vespula* spp., *Vespa* spp., and *Xylocopa* spp. A non-exhaustive list of particular species includes, but is not limited to, *Athalia rosae, Atta texana, Caliroa cerasi, Cimbex americana, Iridomyrmex humilis, Linepithema humile, Mellifera Scutellata, Monomorium minimum, Monomorium pharaonis, Neodiprion sertifer, Solenopsis invicta, Solenopsis geminata, Solenopsis molesta, Solenopsis richteryi, Solenopsis xyloni, Tapinoma sessile,* and *Wasmannia auropunctata.*

(10) Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes acinaciformis, Coptotermes curvignathus, Coptotermes frenchi, Coptotermes formosanus, Coptotermes gestroi, Cryptotermes brevis, Heterotermes aureus, Heterotermes tenuis, Incisitermes minor, Incisitermes snyderi, Microtermes obesi, Nasutitermes corniger, Odontotermes formosanus, Odontotermes obesus, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus.*

(11) Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Nemapogon* spp., *Peridroma* spp., *Phyllonorycter* spp., *Pseudaletia* spp., *Plutella* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Corcyra cephalonica, Cossus cossus, Cydia caryana, Cydia funebrana, Cydia molesta, Cydia nigricana, Cydia pomonella, Darna diducta, Diaphania nitidalis, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Estigmene acrea, Eupoecilia ambiguella, Euxoa auxiliaris, Galleria mellonella, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Manduca sexta, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Phyllonorycter blancardella, Pieris rapae, Plathypena scabra, Platynota idaeusalis, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tinea pellionella, Tineola bisselliella, Trichoplusia ni, Tuta absoluta, Zeuzera coffeae,* and *Zeuzea pyrina.*

(12) Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis.*

(13) Order Orthoptera. A non-exhaustive list of particular genera includes, but is not limited to, *Melanoplus* spp. and *Pterophylla* spp. A non-exhaustive list of particular species includes, but is not limited to, *Acheta domesticus, Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata.*

(14) Order Psocoptera. A non-exhaustive list of particular species includes, but is not limited to, *Liposcelis decolor, Liposcelis entomophila, Lachesilla quercus,* and *Trogium pulsatorium.*

(15) Order Siphonaptera. A non-exhaustive list of particular species includes, but is not limited to, *Ceratophyllus gallinae, Ceratophyllus niger, Ctenocephalides canis, Ctenocephalides felis,* and *Pulex irritans.*

(16) Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular species includes, but is not limited to, *Caliothrips phaseoli, Frankliniella bispinosa, Frankliniella fusca, Frankliniella occidentalis, Frankliniella schultzei, Frankliniella tritici, Frankliniella williamsi, Heliothrips haemorrhoidalis, Rhipiphorothrips cruentatus, Scirtothrips citri, Scirtothrips dorsalis, Taeniothrips rhopalantennalis, Thrips hawaiiensis, Thrips nigropilosus, Thrips orientalis, Thrips palmi*, and *Thrips tabaci*.

(17) Order Thysanura. A non-exhaustive list of particular genera includes, but is not limited to, *Lepisma* spp. and *Thermobia* spp.

(18) Order Acarina. A non-exhaustive list of particular genera includes, but is not limited to, *Acarus* spp., *Aculops* spp., *Argus* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Liponyssoides sanguineus, Notoedres cati, Oligonychus coffeae, Oligonychus ilicis, Ornithonyssus bacoti, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae, Tyrophagus longior*, and *Varroa destructor*.

(19) Order Araneae. A non-exhaustive list of particular genera includes, but is not limited to, *Loxosceles* spp., *Latrodectus* spp., and *Atrax* spp. A non-exhaustive list of particular species includes, but is not limited to, *Loxosceles reclusa, Latrodectus mactans*, and *Atrax robustus*.

(20) Class Symphyla. A non-exhaustive list of particular species includes, but is not limited to, *Scutigerella immaculata*.

(21) Subclass Collembola. A non-exhaustive list of particular species includes, but is not limited to, *Bourletiella hortensis, Onychiurus armatus, Onychiurus fimetarius*, and *Sminthurus viridis*.

(22) Phylum Nematoda. A non-exhaustive list of particular genera includes, but is not limited to, *Aphelenchoides* spp., *Belonolaimus* spp., *Criconemella* spp., *Ditylenchus* spp., *Globodera* spp., *Heterodera* spp., *Hirschmanniella* spp., *Hoplolaimus* spp., *Meloidogyne* spp., *Pratylenchus* spp., and *Radopholus* spp. A non-exhaustive list of particular species includes, but is not limited to, *Dirofilaria immitis, Globodera pallida, Heterodera glycines, Heterodera zeae, Meloidogyne incognita, Meloidogyne javanica, Onchocerca volvulus, Pratylenchus penetrans, Radopholus similis*, and *Rotylenchulus reniformis*.

(23) Phylum Mollusca. A non-exhaustive list of particular species includes, but is not limited to, *Arlon vulgaris, Cornu aspersum, Deroceras reticulatum, Limax flavus, Milax gagates*, and *Pomacea canaliculata*.

A particularly preferred pest group to control is sap-feeding pests. Sap-feeding pests, in general, have piercing and/or sucking mouthparts and feed on the sap and inner plant tissues of plants. Examples of sap-feeding pests of particular concern to agriculture include, but are not limited to, aphids, leafhoppers, scales, *thrips*, psyllids, planthoppers, mealybugs, stinkbugs, and whiteflies. Specific examples of Orders that have sap-feeding pests of concern in agriculture include but are not limited to, Anoplura and Hemiptera. Specific examples of Hemiptera that are of concern in agriculture include, but are not limited to, *Aulacaspis* spp., *Aphrophora* spp., *Aphis* spp., *Bemisia* spp., *Coccus* spp., *Euschistus* spp., *Lygus* spp., *Macrosiphum* spp., *Nezara* spp., *Rhopalosiphum* spp., *Sogatella* spp., *Nilaparvata* spp., *Laodelphax* spp., and *Nephotettix* spp.

Another particularly preferred pest group to control is chewing pests. Chewing pests, in general, have mouthparts that allow them to chew on the plant tissue including roots, stems, leaves, buds, and reproductive tissues (including, but not limited to flowers, fruit, and seeds). Examples of chewing pests of particular concern to agriculture include, but are not limited to, caterpillars, beetles, grasshoppers, and locusts. Specific examples of Orders that have chewing pests of concern in agriculture include but are not limited to, Coleoptera, Lepidoptera, and Orthoptera. Specific examples of Coleoptera that are of concern in agriculture include, but are not limited to, *Anthonomus* spp., *Cerotoma* spp., *Chaetocnema* spp., *Colaspis* spp., *Cyclocephala* spp., *Diabrotica* spp., *Hypera* spp., *Phyllophaga* spp., *Phyllotreta* spp., *Sphenophorus* spp., *Sitophilus* spp.

The phrase "pesticidally effective amount" means the amount of a pesticide needed to achieve an observable effect on a pest, for example, the effects of necrosis, death, retardation, prevention, removal, destruction, or otherwise diminishing the occurrence and/or activity of a pest in a locus. This effect may come about when pest populations are repulsed from a locus, pests are incapacitated in, or around, a locus, and/or pests are exterminated in, or around, a locus. Of course, a combination of these effects can occur. Generally, pest populations, activity, or both are desirably reduced more than fifty percent, preferably more than 90 percent, and most preferably more than 99 percent. In general, a pesticidally effective amount, for agricultural purposes, is from about 0.0001 grams per hectare to about 5000 grams per hectare, preferably from about 0.0001 grams per hectare to about 500 grams per hectare, and it is even more preferably from about 0.0001 grams per hectare to about 50 grams per hectare. Alternatively, about 150 grams per hectare to about 250 grams per hectare may be used against pests.

DETAILED DESCRIPTION OF THIS DISCLOSURE

This document discloses the molecule N-(3-chloro-1-(pyridin-3-yl)-1H-pyrazol-4-yl)-2-(methylsulfonyl)propanamide:

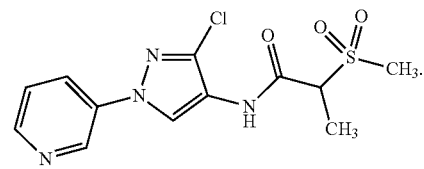 [SMILES: CC(C(=O)Nc1cn(-c2cccnc2)nc1Cl)S(C)(=O)=O]

Formula One also known as F1

Formula One may exist in different geometric or optical isomeric or different tautomeric forms. One or more centers of chirality may be present, in which case Formula One may be present as pure enantiomers, mixtures of enantiomers, pure diastereomers or mixtures of diastereomers. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Centers of tautomerisation may be present. This disclosure covers all such isomers, tautomers, and mixtures thereof, in all proportions. The structures disclosed in the present disclosure may be drawn in only one geometric form for clarity, but are intended to represent all geometric forms of the molecule.

Synthesis of Formula One (F1)

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw, or ACD Name Pro. If such programs are unable to name a molecule, such molecule is named using conventional naming rules. $^1$H NMR spectral data are in ppm ($\delta$) and were recorded at 300, 400, 500, or 600 MHz; $^{13}$C NMR spectral data are in ppm ($\delta$) and were recorded at 75, 100, or 150 MHz; and $^{19}$F NMR spectral data are in ppm ($\delta$) and were recorded at 376 MHz, unless otherwise stated.

A person skilled in the art will recognize that it may be possible to achieve the synthesis of desired molecules by performing some of the steps of the synthetic routes in a different order to that described. A person skilled in the art will also recognize that it may be possible to perform standard functional group interconversions or substitution reactions on desired molecules to introduce or modify substituents.

Example 1: Preparation of 3-chloro-1-(pyridin-3-yl)-1H-pyrazol-4-amine (C5)

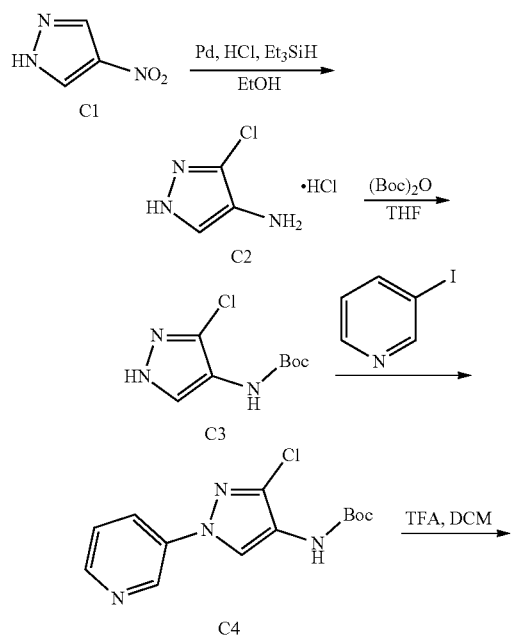

-continued

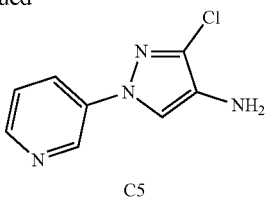

C5

Step 1—Preparation of 3-chloro-1H-pyrazol-4-amine hydrochloride (C2): A 2 liter (L) three-necked round bottom flask was affixed with an overhead stirrer, a temperature probe, an addition funnel, and a nitrogen inlet. Into this three-necked flask were added ethanol (600 milliliters (mL)) and 4-nitro-1H-pyrazole (C1; 50.6 grams (g), 447 millimoles (mmol)). To this solution was added, in one portion, concentrated hydrochloric acid (HCl; 368 mL) (note: rapid exotherm from 15° C. to 39° C.), and the resulting mixture was purged with nitrogen (N$_2$) for 5 minutes (min). Palladium on alumina (5% w/w) (2.6 g) was added, and the mixture was stirred at room temperature while triethylsilane (208 g, 1789 mmol) was added drop-wise over 4 hours (h). The reaction mixture, which started to self-heat slowly from 35° C. to 55° C. over 2 h, was stirred for a total of 16 h. The mixture was vacuum filtered through a plug of Celite®, and a biphasic mixture was collected. The biphasic mixture was transferred to a separatory funnel, and the bottom aqueous layer was collected and rotary evaporated (60° C., 50 mmHg) to dryness with the aid of acetonitrile (3×350 mL). The resulting yellow solid was suspended in acetonitrile (150 mL) and allowed to stand for 2 h at room temperature followed by 1 h at 0° C. in the refrigerator. The solids were filtered and washed with acetonitrile (100 mL) to afford the title compound as a white solid (84 g, 97% yield, 80% purity): mp 190-193° C.; $^1$H NMR (400 MHz, DMSO-d$_6$) $\delta$ 10.46-10.24 (br s, 2H), 8.03 (s, 0.54H), 7.75 (s, 0.46H), 5.95 (br s, 1H); $^{13}$C-NMR (101 MHz, DMSO-d$_6$) $\delta$ 128.24, 125.97, 116.71.

Step 2—Preparation of tert-butyl (3-chloro-1H-pyrazol-4-yl)carbamate (C3): Into a 2 L round bottom flask were added 3-chloro-1H-pyrazol-4-amine hydrochloride (C2; 100 g, 649 mmol) and tetrahydrofuran (THF; 500 mL). To this mixture were added sequentially di-tert-butyl dicarbonate (156 g, 714 mmol), sodium bicarbonate (120 g, 1429 mmol) and water (50.0 mL). The mixture was stirred for 16 h, diluted with water (500 mL) and ethyl acetate (EtOAc; 500 mL) and transferred to a separatory funnel. This gave three layers: a) bottom layer—white gelatinous precipitate; b) middle layer—light yellow aqueous liquid; and c) top layer—auburn organic liquid. The phases were separated, collecting the bottom and middle layers (i.e., aqueous phase) together. The aqueous phase was extracted with EtOAc (2×200 mL), and the organic extracts were combined, washed with brine (200 mL), dried over anhydrous sodium sulfate, filtered and concentrated by rotary evaporation to give a thick auburn-colored oil (160 g). The thick oil was suspended in hexane (1000 mL) and stirred at 55° C. for 2 h. This gave a light brown suspension. The mixture was cooled to 0° C., and the solid was collected by vacuum filtration and rinsed with hexane (2×10 mL). The sample was air dried to constant mass to afford the title compound as a light brown solid (103 g, 72% yield, 80% purity): mp 137-138° C.; $^1$H NMR (400 MHz, CDCl$_3$) $\delta$ 10.69 (s, 1H), 7.91 (s, 1H), 1.52 (s, 9H).

Step 3—Preparation of tert-butyl (3-chloro-1-(pyridin-3-yl)-1H-pyrazol-4-yl)carbamate (C4): A dry 2 L three-necked round bottom flask was equipped with a mechanical stirrer, nitrogen inlet, thermometer, and reflux condenser. Into this flask were added 3-iodopyridine (113 g, 551 mmol), tert-butyl (3-chloro-1H-pyrazol-4-yl)carbamate (C3; 100 g, 459 mmol), powdered potassium phosphate (195 g, 919 mmol), and copper chloride (3.09 g, 23 mmol). Acetonitrile (1 L) and $N^1,N^2$-dimethylethane-1,2-diamine (101 g, 1149 mmol) were added sequentially, and the mixture was heated to 81° C. for 4 h. The mixture was cooled to room temperature and filtered through a bed of Celite®. The filtrate was transferred to a 4 L Erlenmeyer flask equipped with a mechanical stirrer and diluted with water until the total volume was about 4 L. The mixture was stirred for 30 min at room temperature and the resulting solid was collected by vacuum filtration. The solid was washed with water and oven dried for several days in vacuo at 40° C. to a constant weight to give the title compound as a tan solid (117.8 g, 87% yield, 80% purity): mp 140-143° C.; $^1$H NMR (400 MHz, CDCl$_3$) δ 8.96 (s, 1H), 8.53 (dd, J=4.7, 1.2 Hz, 1H), 8.36 (s, 1H), 7.98 (ddd, J=8.3, 2.7, 1.4 Hz, 1H), 7.38 (dd, J=8.3, 4.8 Hz, 1H), 6.37 (s, 1H), 1.54 (s, 9H); ESIMS m/z 338 ([M-t-Bu]$^+$), 220 ([M-O-t-Bu]$^-$).

Step 4—Preparation of 3-chloro-1-(pyridin-3-yl)-1H-pyrazol-4-amine (C5): Trifluoroacetic acid (TFA; 6.79 mL) was added to tert-butyl (3-chloro-1-(pyridin-3-yl)-1H-pyrazol-4-yl)carbamate (C4; 2 g, 6.79 mmol) in dichloromethane (DCM; 6.79 mL), and the mixture was stirred at room temperature for 2 h. Toluene (12 mL) was added, and the reaction mixture was concentrated in vacuo to near dryness. The concentrated reaction mixture was poured into a separatory funnel containing saturated aqueous sodium bicarbonate and was extracted with DCM (3×10 mL). The combined organic layers were concentrated to give the title compound as a white solid (0.954 g, 72%): mp 137.9-139.9° C.; $^1$H NMR (400 MHz, CDCl$_3$) δ 8.84 (d, J=2.4 Hz, 1H), 8.50 (dd, J=4.7, 1.4 Hz, 1H), 7.95 (ddd, J=8.3, 2.7, 1.5 Hz, 1H), 7.52 (s, 1H), 7.37 (ddd, J=8.4, 4.7, 0.7 Hz, 1H), 3.18 (s, 2H); ESIMS m/z 196 ([M+H]$^+$).

Example 2: Preparation of N-(3-chloro-1-(pyridin-3-yl)-1H-pyrazol-4-yl)-2-(methylsulfonyl)propanamide (Formula One)

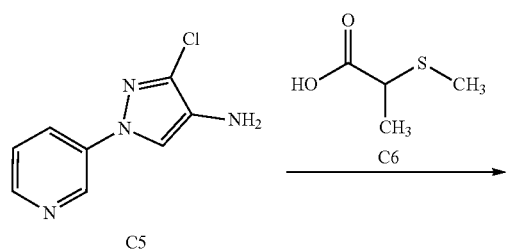

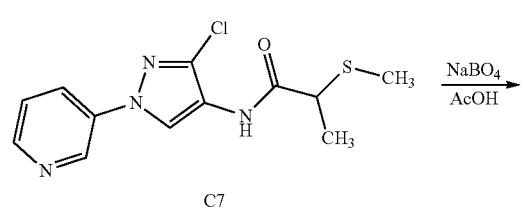

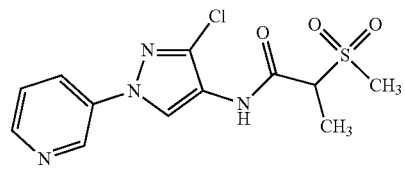

Formula One

Step 1—Preparation of N-(3-chloro-1-(pyridin-3-yl)-1H-pyrazol-4-yl)-2-(methylthio)propanamide (C7): To a suspension of 3-chloro-1-(pyridin-3-yl)-1H-pyrazol-4-amine (C5; 0.1 g, 0.514 mmol) and 2-(methylthio)propanoic acid (C6; 0.185 g, 1.541 mmol) in DCM (1.713 mL) were added sequentially N,N-dimethylpyridin-4-amine (0.220 g, 1.798 mmol) and N1-((ethylimino)methylene)-N3,N3-dimethyl-propane-1,3-diamine hydrochloride (0.305 g, 1.593 mmol). The reaction mixture was stirred at ambient temperature for 18 h and was concentrated. Purification by silica gel chromatography (0-100% EtOAc/hexanes) gave the title compound as a white solid (116 mg, 72%): mp 129-132° C.; $^1$H NMR (400 MHz, CDCl$_3$) δ 8.98 (d, J=2.4 Hz, 1H), 8.63 (s, 1H), 8.58-8.53 (m, 1H), 8.03-7.96 (m, 1H), 7.43-7.37 (m, 1H), 3.59-3.48 (m, 1H), 2.18 (s, 3H), 1.59 (d, J=7.3 Hz, 3H); ESIMS m/z 297 ([M+1]$^+$).

Step 2—Preparation of N-(3-chloro-1-(pyridin-3-yl)-1H-pyrazol-4-yl)-2-(methylsulfonyl)propanamide (Formula One): To a 100 mL round bottom flask were added N-(3-chloro-1-(pyridin-3-yl)-1H-pyrazol-4-yl)-2-(methylthio)propanamide (C7; 882 mg, 2.97 mmol), acetic acid (6.0 mL), and sodium perborate tetrahydrate (915 mg, 5.94 mmol). The reaction mixture was stirred overnight under inert atmosphere in a heating block warmed to 50° C. The reaction mixture was then poured into a brine solution and extracted with DCM (3×20 mL). The combined organic extracts were dried over magnesium sulfate, filtered and concentrated. Purification of the resulting residue by silica gel chromatography (0-10% methanol in DCM) gave the title compound as a white foam (734 mg, 74%): $^1$H NMR (400 MHz, DMSO-d$_6$) δ 10.41 (s, 1H), 9.07 (d, J=2.7 Hz, 1H), 8.94 (s, 1H), 8.55 (dd, J=4.7, 1.4 Hz, 1H), 8.23 (ddd, J=8.4, 2.8, 1.4 Hz, 1H), 7.55 (ddd, J=8.4, 4.8, 0.7 Hz, 1H), 4.41 (q, J=7.0 Hz, 1H), 3.07 (s, 3H), 1.57 (d, J=7.1 Hz, 3H); ESIMS m/z 329 ([M+H]$^+$); IR (thin film) 1680 cm$^{-1}$.

Synthesis of Comparative Molecules

Example 3: Preparation of 3-chloro-N-methyl-1-(pyridin-3-yl)-1H-pyrazol-4-amine (C9)

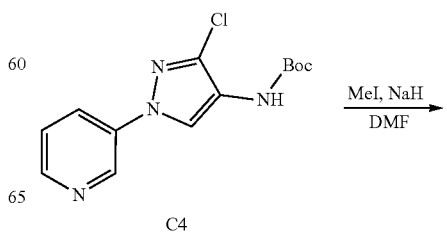

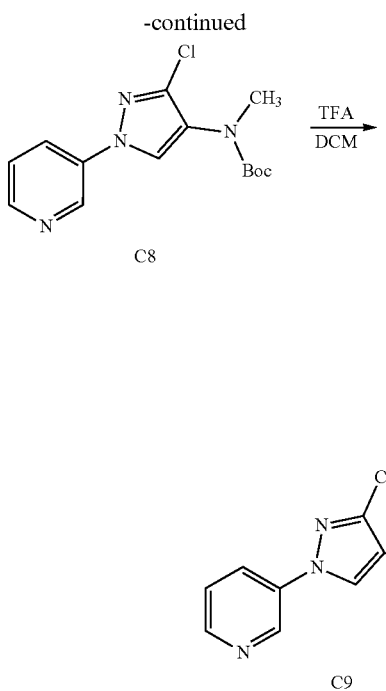

C8

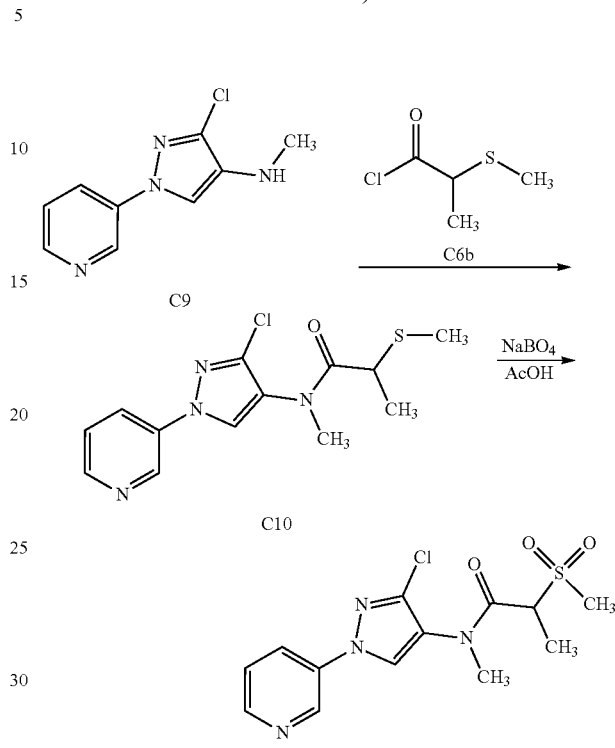

Example 4: Preparation of N-(3-chloro-1-(pyridin-3-yl)-1H-pyrazol-4-yl)-N-methyl-2-(methylsulfonyl)propanamide (Comparative Example 1 Also Known as CE1)

Comparative Example 1

Step 1—Preparation of tert-butyl (3-chloro-1-(pyridin-3-yl)-1H-pyrazol-4-yl)(methyl)carbamate (C8): To a solution of tert-butyl 3-chloro-1-(pyridin-3-yl)-1H-pyrazol-4-ylcarbamate (C4; 1.0 g, 3.39 mmol) in N,N-dimethylformamide (16.96 mL) at 0° C. was added sodium hydride (0.163 g, 4.07 mmol). After 30 min the flask was warmed to ambient temperature and the reaction mixture was stirred for another 30 min. Iodomethane (0.232 mL, 3.73 mmol) was added to the flask, and the reaction mixture was stirred at ambient temperature for 2 h. The reaction was quenched by adding saturated ammonium chloride. The reaction mixture was extracted twice with tert-butyl methyl ether. The organic layer was dried over sodium sulfate, filtered and concentrated. Purification via silica column chromatography (0-100% EtOAc/hexanes) gave the title compound as a yellow oil (983 mg, 94%): $^1$H NMR (400 MHz, CDCl$_3$) δ 8.91 (d, J=2.5 Hz, 1H), 8.64-8.48 (m, 1H), 8.01 (d, J=7.5 Hz, 1H), 7.90 (s, 1H), 7.41 (dd, J=8.3, 4.8 Hz, 1H), 3.23 (s, 3H), 1.58-1.25 (m, 9H); ESIMS m/z 309 ([M+H]$^+$); IR (thin film) 1693 cm$^{-1}$.

Step 2—Preparation of 3-chloro-N-methyl-1-(pyridin-3-yl)-1H-pyrazol-4-amine (C9): To tert-butyl 3-chloro-1-(pyridin-3-yl)-1H-pyrazol-4-yl(methyl)carbamate (C8; 1.65 g, 5.34 mmol) in DCM (5.4 mL) was added trifluoroacetic acid (TFA; 5.4 mL) and the solution was stirred at room temperature for 1 h. Toluene was added and the reaction mixture was concentrated in vacuo to near dryness. The concentrated reaction mixture was poured into a separatory funnel containing saturated sodium bicarbonate and the mixture was extracted with EtOAc (3×20 mL). The extracts were combined, dried over magnesium sulfate, filtered, and concentrated to dryness. The title compound was isolated as a pale yellow solid (0.92 g, 83%): mp 108-118° C.; $^1$H NMR (400 MHz, CDCl$_3$) δ 8.88 (d, J=2.4 Hz, 1H), 8.48 (dd, J=4.7, 1.4 Hz, 1H), 7.96 (ddd, J=8.3, 2.7, 1.4 Hz, 1H), 7.41-7.29 (m, 2H), 2.87 (s, 3H); EIMS m/z 208.

Step 1—Preparation of N-(3-chloro-1-(pyridin-3-yl)-1H-pyrazol-4-yl)-N-methyl-2-(methylthio)propanamide (C10): To a solution of 2-(methylthio)propanoic acid (C6; 481 mg, 4.00 mmol) in DCM (6 mL) were added oxalyl dichloride (0.384 mL, 4.40 mmol) and one drop of dimethylformamide. Vigorous bubbling was observed, and stirring was continued for 30 minutes. The crude acyl chloride reaction mixture (C6b) was concentrated in vacuo to near dryness. The concentrated reaction mixture (C6b) was dissolved in DCM (3 mL) and was added slowly (over ~5 min) to an ice-cold solution of 3-chloro-N-methyl-1-(pyridin-3-yl)-1H-pyrazol-4-amine (C9; 417 mg, 2 mmol) and N-ethyl-N-isopropylpropan-2-amine (0.751 mL, 4.40 mmol) in DCM (3 mL). The resulting deep orange solution was slowly warmed to room temperature over 0.5 hour and was stirred at ambient temperature for 1.5 hour. The reaction mixture was quenched by the addition of saturated sodium bicarbonate solution. The reaction mixture was extracted with DCM (3×10 mL). Purification of the residue by silica gel chromatography (0-100% EtOAc/hexane) gave the title compound as a white solid (495 mg, 76%): mp 128-133° C.; $^1$H NMR (400 MHz, CDCl$_3$) δ 8.94 (d, J=2.4 Hz, 1H), 8.62 (d, J=3.8 Hz, 1H), 8.15 (s, 1H), 8.03 (d, J=8.3 Hz, 1H), 7.46 (dd, J=8.3, 4.8 Hz, 1H), 3.34 (q, J=6.8 Hz, 1H), 3.26 (s, 3H), 2.10 (s, 3H), 1.45 (d, J=6.9 Hz, 3H); ESIMS m/z 311 ([M+1]$^+$).

Step 2—Preparation of N-(3-chloro-1-(pyridin-3-yl)-1H-pyrazol-4-yl)-N-methyl-2-(methylsulfonyl)propanamide (Comparative Example 1): To a 20 mL vial were added sequentially N-(3-chloro-1-(pyridin-3-yl)-1H-pyrazol-4-yl)-N-methyl-2-(methylthio)propanamide (C10; 306 mg, 0.985 mmol), acetic acid (2 mL), and sodium perborate tetrahydrate (333 mg, 2.17 mmol). The solution was heated at 65°

C. for 3 h, cooled, and quenched by the slow addition of saturated sodium bicarbonate solution. The solution was extracted with DCM (3×10 mL), and the combined organic extracts were dried, and concentrated. Purification of the resulting mixture by silica gel chromatography (0-10% methanol in DCM) gave the title compound as an off-white solid (221 mg, 62%): $^1$H NMR (400 MHz, CDCl$_3$) δ 8.97 (dd, J=2.7, 0.7 Hz, 1H), 8.64 (dd, J=4.7, 1.5 Hz, 1H), 8.22 (s, 1H), 8.00 (ddd, J=8.4, 2.7, 1.5 Hz, 1H), 7.45 (ddd, J=8.4, 4.8, 0.8 Hz, 1H), 4.14-3.94 (m, 1H), 3.33 (s, 3H), 3.02 (d, J=0.8 Hz, 3H), 1.65 (d, J=7.0 Hz, 3H); ESIMS m/z 343 ([M+1]$^+$); IR (thin film) 1657 cm$^{-1}$.

Example 5: Preparation of N-(3-chloro-1-(pyridin-3-yl)-1H-pyrazol-4-yl)-N-methyl-2-(methylsulfonyl)acetamide (Comparative Example 2 Also Known as CE2)

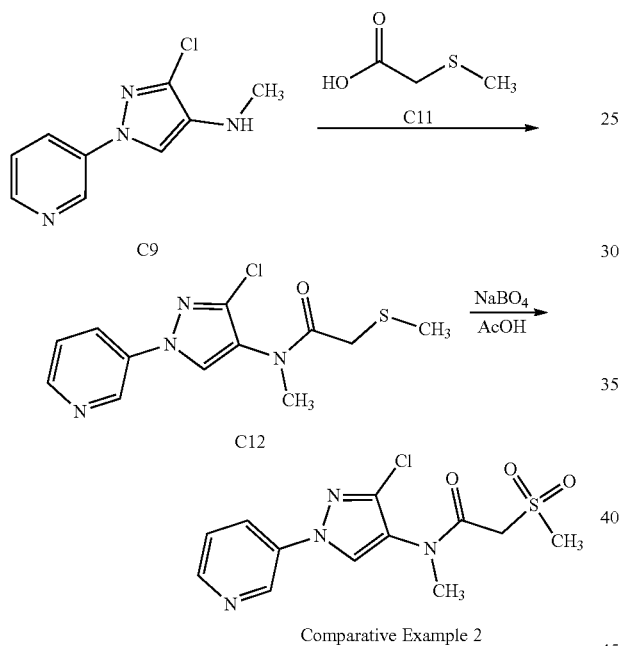

Comparative Example 2

Step 1—Preparation of N-(3-chloro-1-(pyridin-3-yl)-1H-pyrazol-4-yl)-N-methyl-2-(methylthio)acetamide (C12): To a 20 mL vial were added sequentially 3-chloro-N-methyl-1-(pyridin-3-yl)-1H-pyrazol-4-amine (C9; 417 mg, 2 mmol), 2-(methylthio)acetic acid (C11; 318 mg, 3 mmol), N1-((ethylimino)methylene)-N3,N3-dimethylpropane-1,3-diamine hydrochloride (767 mg, 4 mmol), N,N-dimethylpyridin-4-amine (611 mg, 5 mmol), and dichloroethane (6 mL). The solution was stirred at room temperature for 18 h and concentrated. Purification by silica gel chromatography (0-100% EtOAc/hexanes) provided the title compound as pale yellow oil (517 mg, 83%): $^1$H NMR (400 MHz, CDCl$_3$) δ 8.95 (d, J=2.5 Hz, 1H), 8.62 (dd, J=4.8, 1.4 Hz, 1H), 8.13 (s, 1H), 8.04 (ddd, J=8.3, 2.7, 1.4 Hz, 1H), 7.50-7.43 (m, 1H), 3.26 (s, 3H), 3.12 (s, 2H), 2.24 (s, 3H); $^{13}$C NMR (101 MHz, CDCl$_3$) δ 170.00, 148.61, 140.15, 140.03, 135.68, 126.56, 126.42, 125.33, 124.15, 37.16, 34.94, 16.22; ESIMS m/z 297 ([M+H]$^+$).

Step 2—Preparation of N-(3-chloro-1-(pyridin-3-yl)-1H-pyrazol-4-yl)-N-methyl-2-(methylsulfonyl)acetamide (Comparative Example 2): To a 7 mL vial were added sequentially N-(3-chloro-1-(pyridin-3-yl)-1H-pyrazol-4-yl)-N-methyl-2-(methylthio)acetamide (C12; 262 mg, 0.883 mmol), acetic acid (1.5 mL), and sodium perborate tetrahydrate (299 mg, 1.942 mmol). The mixture was stirred at 65° C. for 2 h, then quenched by the addition of saturated sodium bicarbonate solution. The reaction mixture was extracted with DCM (3×10 mL). The combined organic extracts were dried and concentrated. Purification of the resulting mixture by silica gel chromatography (0-10% methanol in DCM) afforded the title compound as a white semi-solid (192 mg, 62.8%): $^1$H NMR (500 MHz, CDCl$_3$) δ 8.97 (d, J=2.6 Hz, 1H), 8.64 (dd, J=4.9, 1.3 Hz, 1H), 8.24 (s, 1H), 8.00 (ddd, J=8.4, 2.8, 1.4 Hz, 1H), 7.45 (dd, J=8.4, 4.8 Hz, 1H), 3.96 (s, 2H), 3.33 (s, 3H), 3.20 (s, 3H); ESIMS m/z 329 ([M+H]$^+$); IR (thin film) 1664 cm$^{-1}$.

Example 6: Preparation of N-(3-chloro-1-(pyridin-3-yl)-1H-pyrazol-4-yl)-2-(methylsulfonyl)acetamide (Formula Two Also Known as CE3)

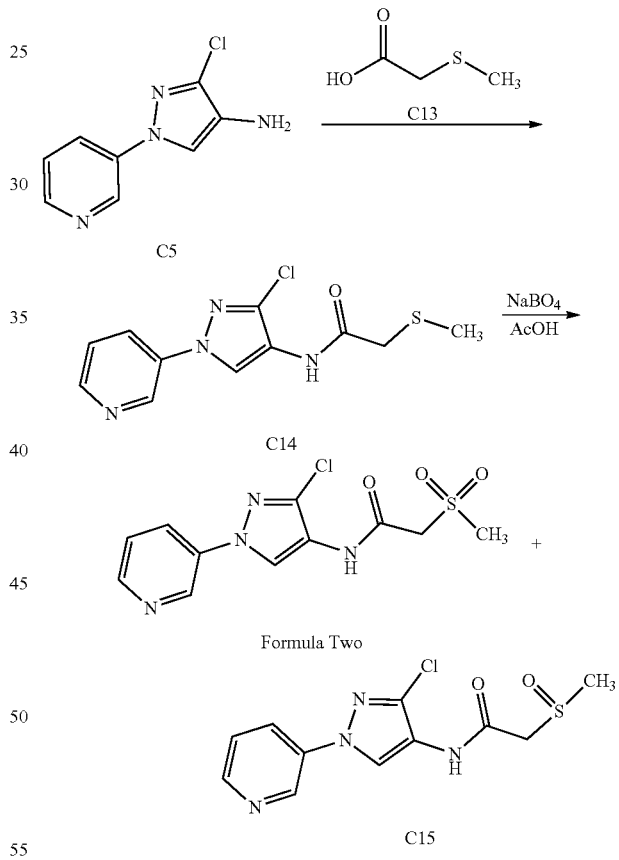

Step 1—Preparation of N-(3-chloro-1-(pyridin-3-yl)-1H-pyrazol-4-yl)-2-(methylthio)acetamide (C14): To a suspension of 3-chloro-1-(pyridin-3-yl)-1H-pyrazol-4-amine (C5; 1.0 g, 5.14 mmol), N,N-dimethylpyridin-4-amine (628 mg, 5.14 mmol), and 2-(methylthio)acetic acid (C13; 654 mg, 6.17 mmol) in dichloroethane (6 mL) was added N1-((ethylimino)methylene)-N3,N3-dimethylpropane-1,3-diamine hydrochloride (1.477 mg, 7.71 mmol). The reaction mixture was stirred at ambient temperature for 24 h. The mixture was diluted with DCM and washed with saturated aqueous ammonium chloride and brine, dried over magnesium sulfate, and concentrated in vacuo to give a brown gum. Purification of the gum by silica gel chromatography (DCM-methanol) gave the title compound as a white solid (1.268 g, 87%): $^1$H NMR (400 MHz, CDCl$_3$) δ 9.06-8.90 (m, 1H), 8.74 (s, 1H), 8.64 (s, 1H), 8.57-8.45 (m, 1H), 8.05-7.90 (m, 1H), 7.46-7.33 (m, 1H), 3.41 (s, 2H), 2.24 (s, 3H); ESIMS m/z 283 ([M+H]$^+$).

Step 2—Preparation of N-(3-chloro-1-(pyridin-3-yl)-1H-pyrazol-4-yl)-2-(methylsulfinyl)acetamide (Formula Two): To solution of N-(3-chloro-1-(pyridin-3-yl)-1H-pyrazol-4-yl)-2-(methylthio)acetamide (C14; 160 mg, 0.566 mmol) in acetic acid (1.5 mL) was added sodium perborate tetrahydrate (183 mg, 1.188 mmol). The reaction mixture was stirred at 60° C. for 2 h. The reaction mixture was cooled and then poured into an excess amount of saturated sodium bicarbonate solution and extracted with DCM. Purification of the resulting residue by silica gel chromatography (0-10% methanol in DCM) gave the title compound as a white solid (101 mg, 53.9%) and N-(3-chloro-1-(pyridin-3-yl)-1H-pyrazol-4-yl)-2-(methylsulfinyl)acetamide (C15) as a white solid (40 mg, 22.5%).

N-(3-Chloro-1-(pyridin-3-yl)-1H-pyrazol-4-yl)-2-(methylsulfonyl)acetamide (Formula Two): $^1$H NMR (300 MHz, CDCl$_3$) δ 8.95 (dd, J=2.7, 0.8 Hz, 1H), 8.66 (d, J=0.6 Hz, 1H), 8.53 (dd, J=4.8, 1.4 Hz, 1H), 8.04 (ddd, J=8.4, 2.7, 1.4 Hz, 1H), 7.45 (ddd, J=8.3, 4.8, 0.7 Hz, 1H), 4.23 (q, J=0.8 Hz, 2H), 3.21 (t, J=0.8 Hz, 3H); ESIMS m/z 315 ([M+H]$^+$); IR (thin film) 1677 cm$^{-1}$.

N-(3-Chloro-1-(pyridin-3-yl)-1H-pyrazol-4-yl)-2-(methylsulfinyl)acetamide (C15): $^1$H NMR (300 MHz, CDCl$_3$) δ 8.95 (dd, J=2.7, 0.8 Hz, 1H), 8.65 (d, J=0.7 Hz, 1H), 8.53 (dd, J=4.8, 1.4 Hz, 1H), 8.04 (ddd, J=8.4, 2.7, 1.5 Hz, 1H), 7.45 (ddd, J=8.4, 4.8, 0.8 Hz, 1H), 3.93 (d, J=13.9 Hz, 1H), 3.71 (d, J=13.8 Hz, 1H), 2.80 (s, 3H); ESIMS m/z 299 ([M+H]$^+$); IR (thin film) 1673 cm$^{-1}$.

Example 7: Preparation of N-(3-chloro-1-(pyridin-3-yl)-1H-pyrazol-4-yl)-2-(methylsulfonyl)acetamide (Formula Three Also Known as CE4)

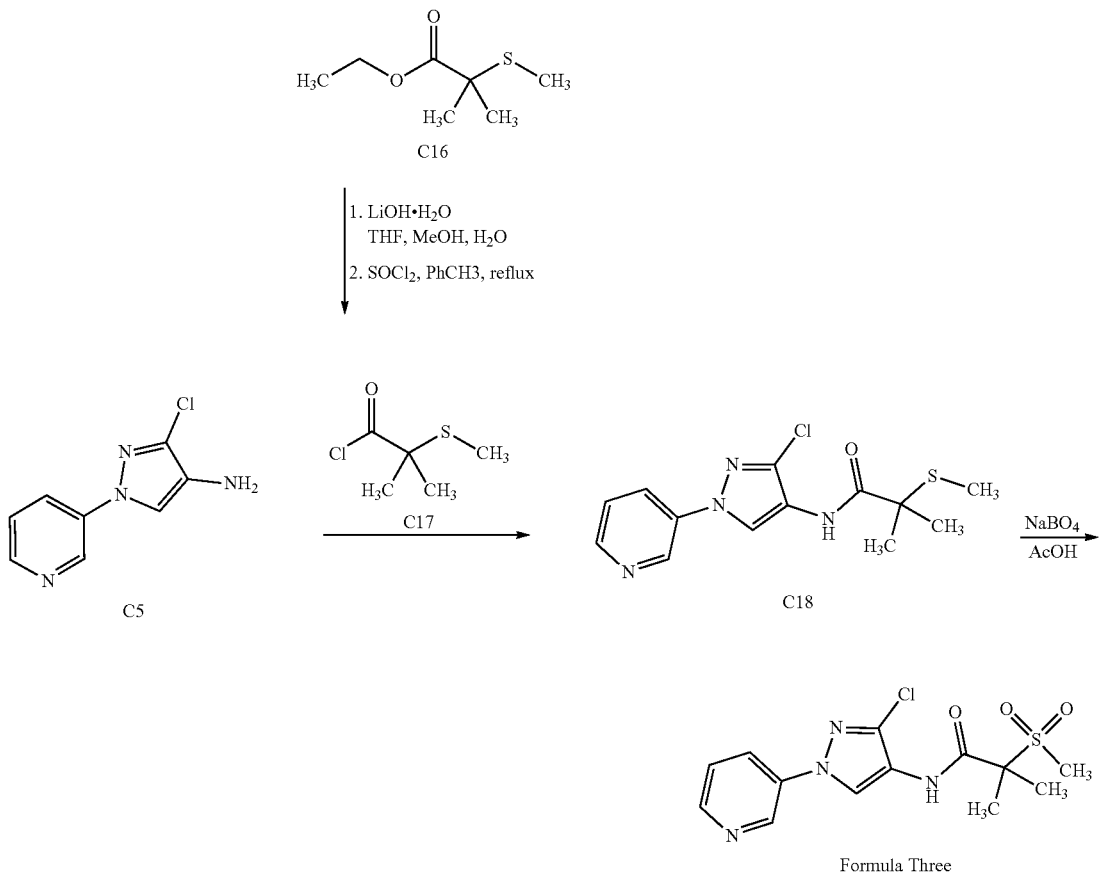

Step 1—Preparation of 2-methyl-2-(methylthio)propanoyl chloride (C17): A 100 mL round bottom flask was charged with ethyl 2-methyl-2-(methylthio)propanoate (C16; 500 mg, 3.08 mmol), lithium hydroxide hydrate (400 mg, 9.53 mmol), THF (6.0 mL), methanol (2.0 mL) and water (2.0 mL). The reaction mixture was allowed to stir at room temperature overnight. The reaction mixture was made acidic with 2 normal (N) HCl and was extracted with EtOAc (3×15 mL). The combined organic extracts were dried over magnesium sulfate, filtered and concentrated.

The title compound can be prepared from the acid above as in Liu, Aiping; Ren, Yeguo; Huang, Lu; Pei, Hui; Hu, Zhibin; Lin, Xuemei; Cheng, Sixi; Huang, Mingzhi; Zhu, Xiaoxing; Wei, Tianlong CN 101928271, 2010. It was isolated (without purification) as a colorless solid (394 mg, 83%): $^1$H NMR (500 MHz, DMSO-d$_6$) δ 2.05 (s, 3H), 1.39 (s, 6H); $^{13}$C NMR (126 MHz, DMSO-d$_6$) δ 174.01, 45.08, 24.31, 11.73; IR (thin film) 3394, 1652, 1204, 1040, 1024, 995 cm$^{-1}$.

Step 2—Preparation of N-(3-chloro-1-(pyridin-3-yl)-1H-pyrazol-4-yl)-2-methyl-2-(methylthio)propanamide (C18): A 50-mL round bottom flask was charged with 2-methyl-2-(methylthio)propanoyl chloride from Step 1 (C17; 200 mg, 1.310 mmol), 3-chloro-1-(pyridin-3-yl)-1H-pyrazol-4-amine (C5; 255 mg, 1.310 mmol) and dichloroethane (6.552 mL). N-Ethyl-N-isopropylpropan-2-amine (4564, 2.62 mmol) was added under inert atmosphere. The reaction mixture was allowed to stir at room temperature for 3 h and was concentrated. The reaction was quenched by pouring into a brine solution, and the reaction mixture was extracted with DCM (2×15 mL). The combined organic extracts were dried over magnesium sulfate, filtered and concentrated. Purification of the resulting residue by silica gel chromatography (0-80% EtOAc/hexanes) gave the title compound as a light orange residue (191 mg, 46.4%): $^1$H NMR (400 MHz, DMSO-d$_6$) δ 9.37 (s, 1H), 9.07 (dd, J=2.8, 0.7 Hz, 1H), 8.78 (s, 1H), 8.55 (dd, J=4.7, 1.4 Hz, 1H), 8.22 (ddd, J=8.3, 2.7, 1.4 Hz, 1H), 7.56 (ddd, J=8.4, 4.8, 0.8 Hz, 1H), 2.10 (s, 3H), 1.53 (s, 6H); $^{13}$C NMR (126 MHz, DMSO-d$_6$) δ 171.99, 147.05, 138.78, 136.62, 134.86, 125.02, 124.85, 123.72, 119.01, 47.13, 24.99, 11.65; IR (thin film) 1675, 1484, 1388, 1353, 947, 800, 702 cm$^{-1}$; ESIMS m/z 311 ([M+H]$^+$).

Step 3—Preparation of N-(3-chloro-1-(pyridin-3-yl)-1H-pyrazol-4-yl)-2-methyl-2-(methylsulfonyl)propanamide (Formula Three): A 25 mL vial was charged with N-(3-chloro-1-(pyridin-3-yl)-1H-pyrazol-4-yl)-2-methyl-2-(methylthio)propanamide (C18; 75 mg, 0.241 mmol), sodium perborate tetrahydrate (74 mg, 0.483 mmol), and acetic acid (2.0 mL) was added. The reaction mixture was stirred in a heating block at 50° C. for 3 h. The reaction mixture was diluted with water (7 mL) and was extracted with DCM (3×7 mL). The combined organic extracts were dried over magnesium sulfate, filtered, and concentrated. Purification of the resulting residue by silica gel chromatography (0-75% EtOAc/hexanes) provided the title compound as a white solid (47 mg, 56.2%): $^1$H NMR (400 MHz, DMSO-d$_6$) δ 9.50 (s, 1H), 9.07 (d, J=2.6 Hz, 1H), 8.83 (s, 1H), 8.56 (dd, J=4.7, 1.4 Hz, 1H), 8.23 (ddd, J=8.4, 2.8, 1.4 Hz, 1H), 7.68-7.49 (m, 1H), 3.10 (s, 3H), 1.66 (s, 6H); $^{13}$C NMR (101 MHz, DMSO-d$_6$) δ 167.92, 148.27, 139.99, 137.59, 135.89, 126.34, 126.09, 124.77, 119.33, 67.49, 36.97, 19.76; IR (thin film) 1678, 1292, 1108, 946, 800, 701 cm$^{-1}$; ESIMS m/z 343 ([M+H]$^+$).

Biological Assays

The following bioassays were conducted against Green Peach Aphid (*Myzus persicae*) and Sweetpotato Whitefly (*Bemisia tabaci*), which are good indicator species for a broad range of sap-feeding pests. The results with these two indicator species show the broad usefulness of the Formula One in controlling sap-feeding insects.

Test Solutions:

F1, CE1, CE2, CE3, and CE4 (2 mg each) were each dissolved in 2 mL of acetone/methanol (1:1) solvent, forming stock solutions of 1000 ppm for each test molecule. The stock solutions were diluted 5× with 0.025% Tween® 20 in water to obtain test solutions at 200 ppm for each test molecule. Subsequent 4× dilutions, in water containing 0.025% Tween® 20 and 10% acetone/methanol (1:1), were used to generate the desired concentrations for dose responses. A minimum of 5 concentrations of each test molecule were used for each assay.

Bioassay 1: Green Peach Aphid (*Myzus persicae*, MYZUPE) ("GPA").

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other crops. GPA also attacks many ornamental crops such as carnation, chrysanthemum, flowering white cabbage, poinsettia, and roses. GPA has developed resistance to many pesticides. Currently, it is a pest that has the third largest number of reported cases of insect resistance (Sparks et al.). Consequently, because of the above factors control of this pest is important. Furthermore, molecules that control this pest (GPA), which is known as a sap-feeding pest, are useful in controlling other pests that feed on the sap from plants.

Test solutions of Formula One and the Comparative Examples, prepared as described above, were tested against GPA using the following procedure.

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. A hand-held aspirator-type sprayer was used for spraying a solution to both sides of cabbage leaves until runoff. Reference plants (solvent check) were sprayed with the diluent only (0.025% Tween® 20 and 10% acetone/methanol (1:1) in water). Treated plants were held in a holding room for three days at approximately 25° C. and ambient relative humidity (RH) prior to grading. Evaluation was conducted by counting the number of live aphids per plant under a microscope three days after treatment. Percent control was measured using Abbott's correction formula (W. S. Abbott, "A Method of Computing the Effectiveness of an Insecticide" J. Econ. Entomol. 18 (1925), pp. 265-267) as follows:

$$\text{Corrected \% Control} = 100 * (X - Y)/X$$

where X=No. of live aphids on solvent check plants and Y=No. of live aphids on treated plants. The results are given in Table 2 below.

Bioassay 2: Sweetpotato Whitefly (*Bemisia tabaci*, BEMITA) ("SPW").

Sweetpotato Whitefly is a major destructive pest to cotton. It is also a serious pest to many vegetable crops, such as melons, cole crops, tomatoes, and head lettuce, as well as ornamental plants. SPW causes damage both through direct feeding damage and virus transmission. SPW is a sap-feeding insect, and its feeding removes nutrients from the plant. This may result in stunted growth, defoliation, reduced yields, and boll shed in cotton. SPW produces large quantities of honeydew, which supports the growth of sooty molds on the plant leaves. SPW is also a vector for viruses, such as cotton leaf crumple virus and tomato yellow leaf curl virus.

Test solutions of Formula One and the Comparative Examples, prepared as described above, were tested against SPW using the following procedure.

Cotton seedlings grown in 3-inch pots, pruned so that only one true leaf remained, were used as test substrate. Adult *B. tabaci* were allowed to colonize these plants and lay eggs for 24 hours after which all adults were removed from the plants using compressed air. Plants were monitored for egg development and, when crawler emergence was underway (>25% emergence based on visual examination using a microscope), the plants were sprayed using the test solutions and methods described above for green peach aphids (GPA). Treated plants were held in a holding room at approximately 25° C. and ambient relative humidity (RH) prior to grading. Evaluation was conducted by counting the number of developed 2-3 instar nymphs per plant under a microscope 7-9 days after treatment. Percent control was measured using Abbott's correction formula (W. S. Abbott, "A Method of Computing the Effectiveness of an Insecticide" J. Econ. Entomol. 18 (1925), pp. 265-267) as follows:

Corrected % Control=100*(X−Y)/X where X=No. of live nymphs on solvent check plants and Y=No. of live nymphs on treated plants. The results are given in Table 2 below.

Analysis of Bioassays

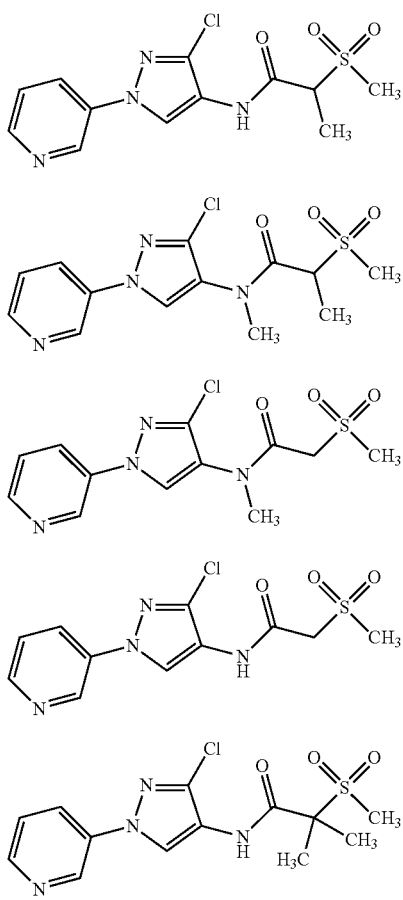

TABLE TWO

| Molecule | # | Bemisia tabaci Mean LC$_{50}$ PPM | % | # | Myzus persicae Mean LC$_{50}$ PPM | % |
|---|---|---|---|---|---|---|
| CE1 | 2 | 5.61 | 15 | 2 | 0.29 | 314 |
| CE2 | 1 | 21.01 | 331 | 2 | 0.52 | 643 |
| F1 | 2 | 4.87 | | 6 | 0.07 | |
| CE3 | 2 | 25.35 | 421 | 3 | 0.05 | −29 |
| CE4 | 2 | 9.72 | 100 | 2 | 2.17 | 3000 |

In Table 2, F1, CE1, CE2, CE3, and CE4, bioassay results are shown. The # column shows the number of replicates of each bioassay conducted. The Mean LC$_{50}$ indicates parts per million. The % column shows the percent increase in the Mean LC$_{50}$ required. For example, in the *Myzus persicae* bioassays, comparing CE4 to F1, the percent increase is ((2.17−0.07)/0.07)*100=3000% which means it take much more of CE4 compared to F1 in order to achieve the same effect.

In light of the above bioassays, the average % of all of the bioassays is ((15+331+421+100+314+643+(−29)+3000)/8) which is about 599%. This indicates that on average about 599% more pesticide is require in order to be as effective as F1. This is unexpected considering the molecules tested.

Agriculturally Acceptable Acid Addition Salts, Salt Derivatives, Solvates, Ester Derivatives, Polymorphs, Isotopes, and Radionuclides Formula One may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids.

Formula One may be formulated into salt derivatives. By way of a non-limiting example, a salt derivative may be prepared by contacting a free base with a sufficient amount of the desired acid to produce a salt. A free base may be regenerated by treating the salt with a suitable dilute aqueous base solution such as dilute aqueous sodium hydroxide, potassium carbonate, ammonia, and sodium bicarbonate. As an example, in many cases, a pesticide such as 2,4-D is made more water-soluble by converting it to its dimethylamine salt.

Formula One may be formulated into stable complexes with a solvent, such that the complex remains intact after the non-complexed solvent is removed. These complexes are often referred to as "solvates." However, it is particularly desirable to form stable hydrates with water as the solvent.

Formula One may be made as various crystal polymorphs. Polymorphism is important in the development of agrochemicals since different crystal polymorphs or structures of the same molecule can have vastly different physical properties and biological performances.

Formula One may be made with different isotopes. Of particular importance are molecules having $^{2}H$ (also known as deuterium) or $^{3}H$ (also known as tritium) in place of $^{1}H$. Formula One may be made with different radionuclides. Of particular importance are molecules having $^{14}C$ (also known as radiocarbon). Formula One having deuterium, tritium, or $^{14}C$ may be used in biological studies allowing tracing in chemical and physiological processes and half-life studies, as well as, MoA studies.

Combinations

In another embodiment of this invention, Formula One may be used in combination (such as, in a compositional mixture, or a simultaneous or sequential application) with one or more active ingredients.

In another embodiment of this invention, Formula One may be used in combination (such as, in a compositional mixture, or a simultaneous or sequential application) with one or more active ingredients each having a MoA that is the same as, similar to, or, preferably, different from, the MoA of Formula One.

In another embodiment, Formula One may be used in combination (such as, in a compositional mixture, or a simultaneous or sequential application) with one or more molecules having acaricidal, algicidal, avicidal, bactericidal, fungicidal, herbicidal, insecticidal, molluscicidal, nematicidal, rodenticidal, and/or virucidal properties.

In another embodiment, Formula One may be used in combination (such as, in a compositional mixture, or a simultaneous or sequential application) with one or more molecules that are antifeedants, bird repellents, chemosterilants, herbicide safeners, insect attractants, insect repellents, mammal repellents, mating disrupters, plant activators, plant growth regulators, plant health stimulators or promoters, nitrification inhibitors, and/or synergists.

In another embodiment, Formula One may also be used in combination (such as in a compositional mixture, or a simultaneous or sequential application) with one or more biopesticides.

In another embodiment, in a pesticidal composition combinations of Formula One and an active ingredient may be used in a wide variety of weight ratios. For example, in a two-component mixture, the weight ratio of Formula One to an active ingredient, the weight ratios in Table 3 may be used. However, in general, weight ratios less than about 10:1 to about 1:10 are preferred.

TABLE 3

| Weight Ratios Formula One:active ingredient |
|---|
| 100:1 to 1:100 |
| 50:1 to 1:50 |
| 20:1 to 1:20 |
| 10:1 to 1:10 |
| 5:1 to 1:5 |
| 3:1 to 1:3 |
| 2:1 to 1:2 |
| 1:1 |

Weight ratios of a molecule of Formula One to an active ingredient may also be depicted as X:Y; wherein X is the parts by weight of Formula One and Y is the parts by weight of the active ingredient. The numerical range of the parts by weight for X is $0<X\leq 100$ and the parts by weight for Y is $0<Y\leq 100$ and is shown graphically in Table 4. By way of non-limiting example, the weight ratio of Formula One to an active ingredient may be 20:1.

Ranges of weight ratios of Formula One to an active ingredient may be depicted as $X_1:Y_1$ to $X_2:Y_2$, wherein X and Y are defined as above.

In one embodiment, the range of weight ratios may be $X_1:Y_1$ to $X_2:Y_2$, wherein $X_1>Y_1$ and $X_2<Y_2$. By way of non-limiting example, the range of a weight ratio of Formula One to an active ingredient may be between 3:1 and 1:3, inclusive of the endpoints.

In another embodiment, the range of weight ratios may be $X_1:Y_1$ to $X_2:Y_2$, wherein $X_1>Y_1$ and $X_2>Y_2$. By way of non-limiting example, the range of weight ratio of Formula One to an active ingredient may be between 15:1 and 3:1, inclusive of the endpoints.

In another embodiment, the range of weight ratios may be $X_1:Y_1$ to $X_2:Y_2$, wherein $X_1<Y_1$ and $X_2<Y_2$. By way of non-limiting example, the range of weight ratios of Formula One to an active ingredient may be between about 1:3 and about 1:20, inclusive of the endpoints.

Formulations

A pesticide is often not suitable for application in its pure form. It is usually necessary to add other substances so that the pesticide may be used at the required concentration and in an appropriate form, permitting ease of application, handling, transportation, storage, and maximum pesticidal activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions.

Pesticides are applied most often as aqueous suspensions or emulsions prepared from concentrated formulations of such pesticides. Such water-soluble, water-suspendable, or emulsifiable formulations may be solids usually known as wettable powders, water dispersible granules, liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

TABLE 4

| active ingredient (Y) Parts by weight | | | | | | | | | | |
|---|---|---|---|---|---|---|---|---|---|---|
| | 100 | X, Y | | X, Y | | | X, Y | | | |
| | 50 | X, Y | X, Y | X, Y | | | X, Y | X, Y | | |
| | 20 | X, Y | | X, Y | X, Y | | X, Y | | X, Y | |
| | 15 | X, Y | X, Y | | | | X, Y | X, Y | X, Y | |
| | 10 | X, Y | | X, Y | | | | | | |
| | 5 | X, Y | X, Y | X, Y | | | X, Y | | | |
| | 3 | X, Y | X, Y | | X, Y | X, Y | X, Y | X, Y | X, Y | |
| | 2 | X, Y | | X, Y | X, Y | | X, Y | X, Y | | |
| | 1 | X, Y | X, Y | X, Y | X, Y | X, Y | X, Y | X, Y | X, Y | X, Y |
| | | 1 | 2 | 3 | 5 | 10 | 15 | 20 | 50 | 100 |
| | | Formula One, also known as F1, (X) Parts by weight | | | | | | | | |

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may, also be added to increase the density and viscosity of the aqueous carrier. It is often most effective to grind and mix the pesticide at the same time by preparing the aqueous mixture and homogenizing it in an implement such as a sand mill, ball mill, or piston-type homogenizer. The pesticide in suspension might be microencapsulated in plastic polymer.

Oil dispersions (OD) comprise suspensions of organic solvent-insoluble pesticides finely dispersed in a mixture of organic solvent and emulsifiers at a concentration in the range from about 2% to about 50% by weight. One or more pesticides might be dissolved in the organic solvent. Useful organic solvents include aromatics, especially xylenes and petroleum fractions, especially the high-boiling naphthalenic and olefinic portions of petroleum such as heavy aromatic naphtha. Other solvents may include vegetable oils, seed oils, and esters of vegetable and seed oils. Suitable emulsifiers for oil dispersions are selected from conventional anionic and non-ionic surfactants. Thickeners or gelling agents are added in the formulation of oil dispersions to modify the rheology or flow properties of the liquid and to prevent separation and settling of the dispersed particles or droplets.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier, which has been pre-formed to the appropriate particle size, in the range of from about 0.5 mm to about 3 mm. Such compositions may also be formulated by making a dough or paste of the carrier and molecule, and then crushing and drying to obtain the desired granular particle size. Another form of granules is a water emulsifiable granule (EG). It is a formulation consisting of granules to be applied as a conventional oil-in-water emulsion of the active ingredient(s), either solubilized or diluted in an organic solvent, after disintegration and dissolution in water. Water emulsifiable granules comprise one or several active ingredient(s), either solubilized or diluted in a suitable organic solvent that is (are) absorbed in a water soluble polymeric shell or some other type of soluble or insoluble matrix.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. Dusts may be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions, the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait, they also consume the pesticide. Baits may take the form of granules, gels, flowable powders, liquids, or solids. Baits may be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings, or in special chambers.

Pesticides may be microencapsulated by suspending the pesticide particles or droplets in polymers of various types. By altering the chemistry of the polymer or by changing factors in the processing, microcapsules may be formed of various sizes, solubility, wall thicknesses, and degrees of penetrability. These factors govern the speed with which the active ingredient within is released, which in turn, affects the residual performance, speed of action, and odor of the product. The microcapsules might be formulated as suspension concentrates or water dispersible granules.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one molecule which is agriculturally active, and is individually coated with a monolamellar or oligolamellar layer comprising: (1) at least one non-ionic lipophilic surface-active agent, (2) at least one non-ionic hydrophilic surface-active agent, and (3) at least one ionic surface-active agent, wherein the globules having a mean particle diameter of less than 800 nanometers.

Other Formulation Components

Generally, when Formula One is used in a formulation, such formulation can also contain other components. These components include, but are not limited to (this is a non-exhaustive and non-mutually exclusive list), wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate, sodium dioctyl sulfosuccinate, alkyl phenol ethoxylates, and aliphatic alcohol ethoxylates.

A dispersing agent is a substance that adsorbs onto the surface of particles, helps to preserve the state of dispersion of the particles, and prevents them from reaggregating. Dispersing agents are added to agrochemical formulations to facilitate dispersion and suspension during manufacture, and to ensure the particles redisperse into water in a spray tank. They are widely used in wettable powders, suspension concentrates, and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium-naphthalene-sulfonate-formaldehyde-condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates, sodium naphthalene sulfonate formaldehyde condensates, tristyrylphenol-ethoxylate-phosphate-esters, aliphatic alcohol ethoxylates, alkyl ethoxylates, EO-PO block copolymers, and graft copolymers.

An emulsifying agent is a substance that stabilizes a suspension of droplets of one liquid phase in another liquid phase. Without the emulsifying agent, the two liquids would separate into two immiscible liquid phases. The most commonly used emulsifier blends contain an alkylphenol or an aliphatic alcohol with twelve or more ethylene oxide units and the oil-soluble calcium salt of dodecylbenzenesulfonic acid. A range of hydrophile-lipophile balance ("HLB") values from about 8 to about 18 will normally provide good stable emulsions. Emulsion stability can sometimes be improved by the addition of a small amount of an EO-PO block copolymer surfactant.

A solubilizing agent is a surfactant that will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates, linear aliphatic alcohol ethoxylates, and aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules, and water-dispersible granules.

Organic solvents are used mainly in the formulation of emulsifiable concentrates, oil-in-water emulsions, suspoemulsions, oil dispersions, and ultra-low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, oil dispersions, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate and oil dispersion formulations using clays and silicas. Examples of these types of materials, include, but are not limited to, montmorillonite, bentonite, magnesium aluminum silicate, and attapulgite. Water-soluble polysaccharides in water based suspension concentrates have been used as thickening-gelling agents for many years. The types of polysaccharides most commonly used are natural extracts of seeds and seaweeds or are synthetic derivatives of cellulose. Examples of these types of materials include, but are not limited to, guar gum, locust bean gum, carrageenan, alginates, methyl cellulose, sodium carboxymethyl cellulose (SCMC), and hydroxyethyl cellulose (HEC). Other types of anti-settling agents are based on modified starches, polyacrylates, polyvinyl alcohol, and polyethylene oxide. Another good anti-settling agent is xanthan gum.

Microorganisms can cause spoilage of formulated products. Therefore, preservation agents are used to eliminate or reduce their effect. Examples of such agents include, but are not limited to: propionic acid and its sodium salt, sorbic acid and its sodium or potassium salts, benzoic acid and its sodium salt, p-hydroxybenzoic acid sodium salt, methyl p-hydroxybenzoate, and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

Applications

Formula One may be applied to any locus. Particular loci to apply such molecules include loci where alfalfa, almonds, apples, barley, beans, canola, corn, cotton, crucifers, flowers, fodder species (Rye Grass, Sudan Grass, Tall Fescue, Kentucky Blue Grass, and Clover), fruits, lettuce, oats, oil seed crops, oranges, peanuts, pears, peppers, potatoes, rice, sorghum, soybeans, strawberries, sugarcane, sugarbeets, sunflowers, tobacco, tomatoes, wheat (for example, Hard Red Winter Wheat, Soft Red Winter Wheat, White Winter Wheat, Hard Red Spring Wheat, and Durum Spring Wheat), and other valuable crops are growing or the seeds thereof are going to be planted.

Formula One may also be applied where plants, such as crops, are growing and where there are low levels (even no actual presence) of pests that can commercially damage such plants. Applying such molecules in such locus is to benefit the plants being grown in such locus. Such benefits, may include, but are not limited to: helping the plant grow a better root system; helping the plant better withstand stressful growing conditions; improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

Formula One may be applied with ammonium sulfate when growing various plants as this may provide additional benefits.

Formula One may be applied on, in, or around plants genetically modified to express specialized traits, such as *Bacillus thuringiensis* (for example, Cry1Ab, Cry1Ac, Cry1Fa, Cry1A.105, Cry2Ab, Vip3A, mCry3A, Cry3Ab, Cry3Bb, Cry34Ab1/Cry35Ab1), other insecticidal toxins, or those expressing herbicide tolerance, or those with "stacked" foreign genes expressing insecticidal toxins, herbicide tolerance, nutrition-enhancement, or any other beneficial traits.

Formula One may be applied to the foliar and/or fruiting portions of plants to control pests. Either such molecules will come in direct contact with the pest, or the pest will consume such molecules when eating the plant or while extracting sap or other nutrients from the plant.

Formula One may also be applied to the soil, and when applied in this manner, root and stem feeding pests may be controlled. The roots may absorb such molecules thereby taking it up into the foliar portions of the plant to control above ground chewing and sap feeding pests.

Systemic movement of pesticides in plants may be utilized to control pests on one portion of the plant by applying (for example by spraying a locus) a molecule of Formula One to a different portion of the plant. For example, control of foliar-feeding insects may be achieved by drip irrigation or furrow application, by treating the soil with for example pre- or post-planting soil drench, or by treating the seeds of a plant before planting.

Formula One may be used with baits. Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait.

Formula One may be encapsulated inside, or placed on the surface of a capsule. The size of the capsules can range from nanometer size (about 100-900 nanometers in diameter) to micrometer size (about 10-900 microns in diameter).

Formula One may be applied to eggs of pests. Because of the unique ability of the eggs of some pests to resist certain pesticides, repeated applications of such molecules may be desirable to control newly emerged larvae.

Formula One may be applied as seed treatments. Seed treatments may be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide tolerance, such as "Roundup Ready" seed, or those with "stacked" foreign genes expressing insecticidal toxins, herbicide tolerance, nutrition-enhancement, drought tolerance, or any other beneficial traits. Furthermore, such seed treatments with Formula One may further enhance the ability of a plant to withstand stressful growing conditions better. This results in a healthier, more vigorous plant, which can lead to higher yields at harvest time. Generally, about 0.0025 mg of Formula One per seed to about 2.0 mg of Formula One per seed is useful, amounts of about 0.01 mg of Formula One per seed to about 1.75 mg of Formula One per seed is useful, amounts of 0.1 mg of Formula One per seed to about 1.5 mg of Formula One per seed is useful, amounts of 0.25 mg of Formula One per seed to about 0.75 mg of Formula One per seed is useful. In general, an amount of about 0.5 mg of Formula One per seed in useful.

Formula One may be applied with one or more active ingredients in a soil amendment.

Formula One may be used for controlling endoparasites and ectoparasites in the veterinary medicine sector or in the field of non-human-animal keeping. Such molecules may be applied by oral administration in the form of, for example, tablets, capsules, drinks, granules, by dermal application in the form of, for example, dipping, spraying, pouring on, spotting on, and dusting, and by parenteral administration in the form of, for example, an injection.

Formula One may also be employed advantageously in livestock keeping, for example, cattle, chickens, geese, goats, pigs, sheep, and turkeys. They may also be employed advantageously in pets such as, horses, dogs, and cats. Particular pests to control would be flies, fleas, and ticks that are bothersome to such animals. Suitable formulations are administered orally to the animals with the drinking water or feed. The dosages and formulations that are suitable depend on the species.

Formula One may also be used for controlling parasitic worms, especially of the intestine, in the animals listed above.

Formula One may also be employed in therapeutic methods for human health care. Such methods include, but are limited to, oral administration in the form of, for example, tablets, capsules, drinks, granules, and by dermal application.

Formula One may also be applied to invasive pests. Pests around the world have been migrating to new environments (for such pest) and thereafter becoming a new invasive species in such new environment. Such molecules may also be used on such new invasive species to control them in such new environments.

Plant viruses cause an estimated US$60 billion loss in crop yields worldwide each year. Many plant viruses need to be transmitted by a vector, most often insects, examples of which are leafhoppers and plant hoppers. However, nematodes also have been shown to transmit viruses. Nematodes transmit plant viruses by feeding on roots. Formula One may also be applied to a plant in order to inhibit pests that carry plant virus so that this reduces the chance that such plant viruses are transmitted from the pest to the plant.

Consequently, in light of the above the following additional, non-exhaustive, details (D) are provided.

1D. A molecule having the following formula

Formula One also known as F1 and N-oxides, agriculturally acceptable acid addition salts, salt derivatives, solvates, ester derivatives, polymorphs, isotopes, resolved stereoisomers, and tautomers, thereof.

2D. A composition comprising a molecule according to 1D and further comprising a carrier.

3D. A composition according to 2D said composition further comprising an active ingredient.

4D. A composition according to any of the previous details, said composition further comprising an active ingredient selected from acaricides, algicides, antifeedants, avicides, bactericides, bird repellents, chemosterilants, fungicides, herbicide safeners, herbicides, insect attractants, insect repellents, insecticides, mammal repellents, mating disrupters, molluscicides, nematicides, plant activators, plant health stimulators or promoters, nitrification inhibitors, plant growth regulators, rodenticides, synergists, and virucides.

5D. A composition according to any of the previous details, said composition further comprising an active ingredient selected from AIGA.

6D. A composition according to any of the previous details, said composition further comprising an active ingredient selected from AI-1.

7D. A composition according to any of the previous details, said composition further comprising an active ingredient selected from AI-2.

8D. A composition according to any of the previous details, said composition further comprising Lotilaner.

9D. A composition according to any of the previous details, said composition further comprising a molecule selected from Table A.

10D. A composition according to any of the previous details, said composition further comprising an active ingredient selected from AIGA-2.

11D. A composition according to any of the previous details, said composition further comprising a biopesticide.

12D. A composition according to any of the previous details, said composition further comprising an active ingredient selected from Acetylcholinesterase (AChE) inhibitors.

13D. A composition according to any of the previous details, said composition further comprising an active ingredient selected from GABA-gated chloride channel antagonists.

14D. A composition according to any of the previous details, said composition further comprising an active ingredient selected from Sodium channel modulators.

15D. A composition according to any of the previous details, said composition further comprising an active ingredient selected from Nicotinic acetylcholine receptor (nAChR) agonists.

16D. A composition according to any of the previous details, said composition further comprising an active ingredient selected from Nicotinic acetylcholine receptor (nAChR) allosteric activators.

17D. A composition according to any of the previous details, said composition further comprising an active ingredient selected from Chloride channel activators.

18D. A composition according to any of the previous details, said composition further comprising an active ingredient selected from Juvenile hormone mimics.

19D. A composition according to any of the previous details, said composition further comprising an active ingredient selected from Miscellaneous nonspecific (multi-site) inhibitors.

20D. A composition according to any of the previous details, said composition further comprising an active ingredient selected from Modulators of Chordotonal Organs.

21D. A composition according to any of the previous details, said composition further comprising an active ingredient selected from Mite growth inhibitors.

22D. A composition according to any of the previous details, said composition further comprising an active ingredient selected from Microbial disruptors of insect midgut membranes.

23D. A composition according to any of the previous details, said composition further comprising an active ingredient selected from Inhibitors of mitochondrial ATP synthase.

24D. A composition according to any of the previous details, said composition further comprising an active ingredient selected from Uncouplers of oxidative phosphorylation via disruption of the proton gradient.

25D. A composition according to any of the previous details, said composition further comprising an active ingredient selected from Nicotinic acetylcholine receptor (nAChR) channel blockers.

26D. A composition according to any of the previous details, said composition further comprising an active ingredient selected from Inhibitors of chitin biosynthesis, type 0.

27D. A composition according to any of the previous details, said composition further comprising an active ingredient selected from Inhibitors of chitin biosynthesis, type 1.

28D. A composition according to any of the previous details, said composition further comprising an active ingredient selected from Moulting disruptor, Dipteran.

29D. A composition according to any of the previous details, said composition further comprising an active ingredient selected from Ecdysone receptor agonists.

30D. A composition according to any of the previous details, said composition further comprising an active ingredient selected from Octopamine receptor agonists.

31D. A composition according to any of the previous details, said composition further comprising an active ingredient selected from Mitochondrial complex III electron transport inhibitors.

32D. A composition according to any of the previous details, said composition further comprising an active ingredient selected from Mitochondrial complex I electron transport inhibitors.

33D. A composition according to any of the previous details, said composition further comprising an active ingredient selected from Voltage-dependent sodium channel blockers.

34D. A composition according to any of the previous details, said composition further comprising an active ingredient selected from Inhibitors of acetyl CoA carboxylase.
35D. A composition according to any of the previous details, said composition further comprising an active ingredient selected from Mitochondrial complex IV electron transport inhibitors.
36D. A composition according to any of the previous details, said composition further comprising an active ingredient selected from Mitochondrial complex II electron transport inhibitors.
37D. A composition according to any of the previous details, said composition further comprising an active ingredient selected from Ryanodine receptor modulators.
38D. A composition according to any of the previous details, said composition further comprising an active ingredient selected from Group UN.
39D. A composition according to any of the previous details, said composition further comprising chlorantraniliprole.
40D. A composition according to any of the previous details, said composition further comprising chlorpyrifos.
41D. A composition according to any of the previous details, said composition further comprising cyantraniliprole.
42D. A composition according to any of the previous details, said composition further comprising methomyl.
43D. A composition according to any of the previous details, said composition further comprising methoxyfenozide.
44D. A composition according to any of the previous details, said composition further comprising oxamyl.
45D. A composition according to any of the previous details, said composition further comprising spinetoram.
46D. A composition according to any of the previous details, said composition further comprising spinosad.
47D. A composition according to any of the previous details, said composition further comprising sulfoxaflor.
48D. A composition according to any of the previous details, said composition further comprising triflumezopyrim.
49D. A composition according to any of the previous details, said composition further comprising beta-cyfluthrin.
50D. A composition according to any of the previous details, said composition further comprising clothianidin.
51D. A composition according to any of the previous details, said composition further comprising cyfluthrin.
52D. A composition according to any of the previous details, said composition further comprising flubendiamide.
53D. A composition according to any of the previous details, said composition further comprising fluopyram.
54D. A composition according to any of the previous details, said composition further comprising flupyradifurone.
55D. A composition according to any of the previous details, said composition further comprising imidacloprid.
56D. A composition according to any of the previous details, said composition further comprising spiromesifen.
57D. A composition according to any of the previous details, said composition further comprising spirotetramat.
58D. A composition according to any of the previous details, said composition further comprising spirodiclofen.
59D. A composition according to any of the previous details, said composition further comprising tetraniliprole.
60D. A composition according to any of the previous details, said composition further comprising thiodicarb.
61D. A composition according to any of the previous details, said composition further comprising thiacloprid.
62D. A composition according to any of the previous details, said composition further comprising alpha-cypermethrin.
63D. A composition according to any of the previous details, said composition further comprising cyflumetofen.
64D. A composition according to any of the previous details, said composition further comprising fipronil.
65D. A composition according to any of the previous details, said composition further comprising metaflumizone.
66D. A composition according to any of the previous details, said composition further comprising zeta-cypermethrin.
67D. A composition according to any of the previous details, said composition further comprising afidopyropen.
68D. A composition according to any of the previous details wherein the weight ratio of F1 to an active ingredient is 100:1 to 1:100.
69D. A composition according to any of the previous details wherein the weight ratio of F1 to an active ingredient is 50:1 to 1:50.
70D. A composition according to any of the previous details wherein the weight ratio of F1 to an active ingredient is 20:1 to 1:20.
71D. A composition according to any of the previous details wherein the weight ratio of F1 to an active ingredient is 10:1 to 1:10.
72D. A composition according to any of the previous details wherein the weight ratio of F1 to an active ingredient is 5:1 to 1:5.
73D. A composition according to any of the previous details wherein the weight ratio of F1 to an active ingredient is 3:1 to 1:3.
74D. A composition according to any of the previous details wherein the weight ratio of F1 to an active ingredient is 2:1 to 1:2.
75D. A composition according to any of the previous details wherein the weight ratio of F1 to an active ingredient is 1:1.
76D. A composition according to any of the details wherein the weight ratio of F1 to an active ingredient is X:Y; wherein X is the parts by weight of F1 and Y is the parts by weight of an active ingredient; further wherein the numerical range of the parts by weight for X is $0<X\leq100$ and the parts by weight for Y is $0<Y\leq100$; and further wherein X and Y are selected from Table 4.
77D. A process to control a pest said process comprising applying to a locus a pesticidally effective amount of composition comprising F1.
78D. A process to control a pest said process comprising applying to a locus a pesticidally effective amount of a composition according to any one of the previous details 2D through 76D.
79D. A process according to details 77D or 78D wherein said pest is selected from the group consisting of the group consisting of ants, aphids, bed bugs, beetles, bristletails, caterpillars, cockroaches, crickets, earwigs, fleas, flies, grasshoppers, grubs, leafhoppers, lice, locusts, maggots, mealybugs, mites, nematodes, planthoppers, psyllids, sawflies, scales, silverfish, slugs, snails, spiders, springtails, stink bugs, symphylans, termites, *thrips*, ticks, wasps, whiteflies, and wireworms.
80D. A process according to details 77D or 78D wherein said pest is a sap-feeding pest.
81D. A process according to details 77D or 78D wherein said pest is an aphid.
82D. A process according to details 77D or 78D wherein said pest is a planthopper.
83D. A process according to details 77D or 78D wherein said pest is from the Order Anoplura or Hemiptera.
84D. A process according to details 77D or 78D wherein said composition is applied to the soil.
85D. A process according to details 77D or 78D wherein said composition is applied to the foliar portions of a plant.

86D. A process according to details 77D or 78D wherein said locus rice, corn, soybean, cotton, potato, sorghum, sugarcane, canola, tea, grape, wheat, barley, alfalfa, or other fruits or vegetables are growing.

87D. A composition according to any of the previous details 2D through 76D, said composition further comprising a seed.

88D. A composition according to detail 87D, wherein said seed is a cotton seed, sunflower seed, rice seed, sugarbeet seed, oilseed rape seed, corn seed, wheat seed, barley seed, millet seed, sorghum seed, buckwheat seed, oat seed, rye seed, soybean seed, or quinoa seed.

89D. A composition according to detail 87D wherein about 0.0025 mg of Formula One per seed to about 2.0 mg of Formula One per seed is used.

The headings in this document are for convenience only and must not be used to interpret any portion hereof.

We claim:

1. A composition comprising (a) a molecule of Formula One (F1)

Formula One and (b) an active ingredient selected from the group consisting of 1,3-dichloropropene, chlorpyrifos, hexaflumuron, methomyl, methoxyfenozide, noviflumuron, oxamyl, spinosad, acequinocyl, acetamiprid, acetoprole, avertriflumectin, azinphos-methyl, bifenazate, carbaryl, carbofuran, chlorfenapyr, chlorfluazuron, chromafenozide, clothianidin, cyfluthrin, cypermethrin, deltamethrin, diafenthiuron, endosulfan, esfenvalerate, etoxazole, fipronil, fluacrypyrim, gamma-cyhalothrin, halofenozide, indoxacarb, lufenuron, malathion, novaluron, permethrin, pyridalyl, pyrimidifen, spirodiclofen, tebufenozide, thiacloprid, thiamethoxam, thiodicarb, and tolfenpyrad.

2. The composition according to claim 1, wherein said active ingredient is methomyl.

3. The composition according to claim 1, wherein said active ingredient is methoxyfenozide.

4. The composition according to claim 1, wherein said active ingredient is spinosad.

5. The composition according to claim 1, wherein said active ingredient is acetamiprid.

6. The composition according to claim 1, wherein said active ingredient is clothianidin.

7. The composition according to claim 1, wherein said active ingredient is fipronil.

8. The composition according to claim 1, wherein said active ingredient is indoxacarb.

9. The composition according to claim 1, wherein said active ingredient is thiacloprid.

10. The composition according to claim 1, wherein said active ingredient is thiamethoxam.

11. The composition according to claim 1, wherein the weight ratio of F1 to said active ingredient is 100:1 to 1:100.

12. The composition according to claim 1, wherein said active ingredient is cypermethrin.

13. The composition according to claim 12, wherein said cypermethrin is zeta-cypermethrin.

* * * * *